United States Patent
Studney

(10) Patent No.: US 9,259,303 B2
(45) Date of Patent: Feb. 16, 2016

(54) DENTAL PICK CONTAINER AND DISPENSER

(71) Applicant: Mark A. Studney, Chicago, IL (US)

(72) Inventor: Mark A. Studney, Chicago, IL (US)

( * ) Notice: Subject to any disclaimer, the term of this patent is extended or adjusted under 35 U.S.C. 154(b) by 194 days.

(21) Appl. No.: 13/767,374

(22) Filed: Feb. 14, 2013

(65) Prior Publication Data

US 2014/0224825 A1 Aug. 14, 2014

(51) Int. Cl.
B65D 83/10 (2006.01)
A61C 19/02 (2006.01)
A46B 15/00 (2006.01)
A61C 15/02 (2006.01)

(52) U.S. Cl.
CPC .............. *A61C 19/02* (2013.01); *A46B 15/0093* (2013.01); *A61C 15/02* (2013.01); *A46B 2200/108* (2013.01)

(58) Field of Classification Search
CPC ....................................................... A61C 19/02
USPC ........... 221/232, 1; 206/363, 370, 382, 362.4, 206/63.5, 62.4, 45; 401/183
See application file for complete search history.

(56) References Cited

U.S. PATENT DOCUMENTS

| | | | | |
|---|---|---|---|---|
| 2,063,624 A | * | 12/1936 | Raab ...................... | A45B 19/04 135/24 |
| 3,285,409 A | * | 11/1966 | Loran .................... | A61C 19/02 206/564 |
| 3,343,669 A | * | 9/1967 | Loran .................... | A61C 19/02 206/63.5 |
| 5,505,916 A | * | 4/1996 | Berry, Jr. ................. | A61L 2/26 206/439 |
| 5,664,674 A | * | 9/1997 | Lynch, Jr. .............. | B65D 85/24 206/380 |
| D437,060 S | * | 1/2001 | Mayer ........................ | D24/217 |
| 6,205,611 B1 | * | 3/2001 | Vigil ........................ | A46B 7/04 132/308 |
| 6,923,319 B1 | | 8/2005 | Erickson et al. | |
| 7,044,671 B2 | * | 5/2006 | Parikh et al. ........... | A46B 9/005 401/183 |
| 7,066,349 B2 | | 6/2006 | Cohen | |
| 7,424,952 B2 | * | 9/2008 | Antler .................... | A61C 15/00 132/321 |
| 7,604,146 B2 | | 10/2009 | Maissami | |
| 2003/0196922 A1 | * | 10/2003 | Reaux ............... | A61B 17/06161 206/370 |
| 2005/0255197 A1 | * | 11/2005 | Aldridge ............ | B65D 5/48044 426/108 |
| 2005/0255198 A1 | * | 11/2005 | Aldridge .............. | B65D 5/2057 426/108 |
| 2006/0254609 A1 | | 11/2006 | Kuo | |
| 2008/0228162 A1 | | 9/2008 | Trager et al. | |

FOREIGN PATENT DOCUMENTS

WO WO9407184 A1 3/1994
WO WO2005113067 A2 12/2005

OTHER PUBLICATIONS

International Search Report and Written Opinion, dated Jun. 3, 2014, for PCT Application No. PCT/US2014/016423, 14 pages.

* cited by examiner

*Primary Examiner* — Rakesh Kumar
(74) *Attorney, Agent, or Firm* — Kinney & Lange, P.A.

(57) ABSTRACT

A container for separating, storing, and dispensing dental picks includes a container to receive a sheet of dental picks, wherein the sheet of dental picks includes multiple interconnected dental picks, a separating device to separate the sheet of dental picks into singular dental picks, and a dispensing device to dispense the singular dental picks, one at a time. A method for separating and dispensing dental picks includes obtaining a sheet of dental picks, wherein the sheet of dental picks includes multiple interconnected dental picks, loading the sheet of dental picks into a container, separating the sheet of dental picks into singular dental picks, and dispensing the singular dental picks one at a time.

18 Claims, 17 Drawing Sheets

DENTAL PICK CONTAINER AND DISPENSER

BACKGROUND

The present invention relates to dental picks, and in particular, to a container and dispenser for dental picks.

Dental picks are picks that can be used in a manner similar to a toothpick and in a manner similar to floss. Dental picks are capable of being inserted between two teeth to remove stuck food, bacteria, or other debris. Dental picks are typically made out of molded plastic and include a cylindrical rod with a handle section at a first end of the cylindrical rod, and a second end of the cylindrical rod that gradually tapers to a point. Attached to the second end of the cylindrical rod are soft, flexible bristles. These bristles are typically made out of nylon filaments or a rubber-like elastomer material. The second end of the dental pick with the bristles can be used to clean spaces in the oral cavity in a variety of ways. First, dental picks can be inserted between two teeth to remove stuck food, bacteria, plaque, and other debris. Second, dental picks can be used around implants, bridges, crowns, and other dental devices, to remove any stuck food, bacteria, and other debris. Third, dental picks can be used around orthodontic appliances, including braces, brackets, and permanent retainers, to remove any stuck food, bacteria, or other debris.

Dental picks are typically manufactured and sold in sheets of interconnected dental picks. A sheet of dental picks typically includes several dental picks that are connected to one another at the handle portion. The dental picks can be separated by bending or twisting the sheet to break the dental picks apart from each other. There are disadvantages to snapping and breaking the sheet of dental picks apart in this manner. First, breaking the dental picks apart can be cumbersome and time consuming for the user. Second, after the dental picks have been separated, it can be cumbersome to contain, store, and dispense the dental picks individually. The storage containers that are available today only accommodate bulk sheets of dental picks and therefore create a cumbersome experience for the user. Some storage containers require both hands of the user to open the container, remove a sheet from the container, manually separate one pick from the sheet, and place the remaining sheet back into the container. Alternatively, if all of the dental picks are separated from the sheet at once, it can be cumbersome for the user to carefully align and place the singular dental picks in the container. The user also has to then be careful to retrieve one dental pick at a time without allowing any of the other dental picks to come out of the container.

SUMMARY

According to the present invention, a container for separating, storing and dispensing dental picks includes a container to receive a sheet of multiple interconnected dental picks, a separating device to separate the sheet of dental picks into singular dental picks, and a dispensing device to dispense the singular dental picks, one at a time. A method for separating and dispensing dental picks includes obtaining a sheet of multiple interconnected dental picks, loading the sheet of dental picks into a container, separating the sheet of dental picks into singular dental picks, and dispensing the singular dental picks one at a time.

DETAILED DESCRIPTION

In general, the present invention relates to a device for breaking apart, storing, and dispensing dental picks. Different embodiments of the device separate a sheet of dental picks into singular dental picks by slicing them apart, using pressure to break them apart, or folding the dental picks against each other in an alternating pattern to snap them apart. The dental picks are stored in a container and can be dispensed one-by-one as needed by the user.

Figure 1:
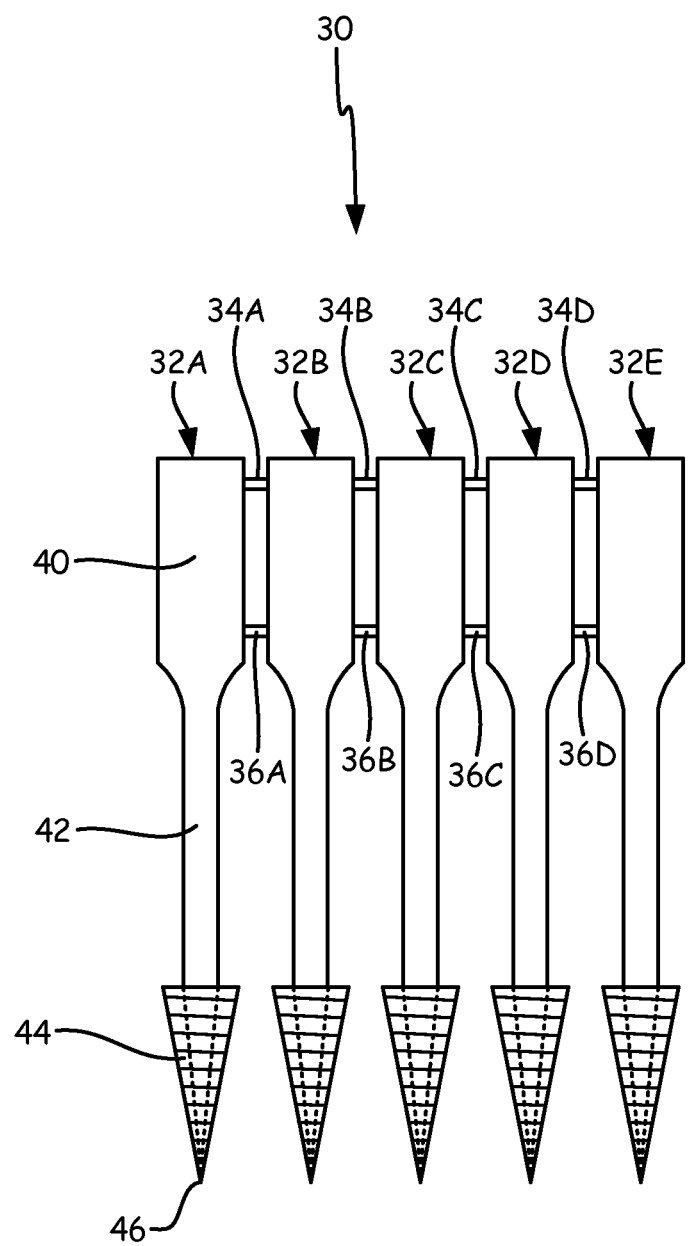
FIG. 1 is a front elevation view of a sheet of dental picks.

FIG. 1 is a front elevation view of sheet 30. Sheet 30 includes a plurality of dental picks 32 (including dental pick 32A, dental pick 32B, dental pick 32C, dental pick 32D, and dental pick 32E), connecting ligaments 34 (including connecting ligament 34A, connecting ligament 34B, connecting ligament 34C, and connecting ligament 34D), and connecting ligaments 36 (including connecting ligament 36A, connecting ligament 36B, connecting ligament 36C, and connecting ligament 36D). Each dental pick 32 includes handle 40, body 42, bristles 44, and tip 46. Sheet 30 includes five dental picks 32 in the embodiment shown, but may include any number of dental picks 32 in alternate embodiments.

In sheet 30, dental pick 32A is connected to dental pick 32B with connecting ligament 34A and connecting ligament 36A; dental pick 32B is connected to dental pick 32C with connecting ligament 34B and connecting ligament 36B; dental pick 32C is connected to dental pick 32D with connecting ligament 34C and connecting ligament 36C; and dental pick 32D is connected to dental pick 32E with connecting ligament 34D and connecting ligament 36D. Connecting ligaments 34 connect handles 40 of dental picks 32 near a top end of handles 40. Connecting ligaments 36 connects handles 40 of dental picks 32 near a bottom end of handles 40. Connecting ligaments 34 and connecting ligaments 36 can be broken when dental picks 32 are separated. In alternate embodiments, connecting ligaments 34 and connecting ligaments 36 can alternate in number and configuration, including using only one connecting ligament or using more than two connecting ligaments. Connecting ligaments 34 and connecting ligaments 36 can also vary in size and shape, for example one long connecting ligament that runs the length of handle 40 could be used between dental picks 32.

Each dental pick 32 includes handle 40 that is attached to body 42. Handle 40 is a flattened piece with a substantially rectangular shape in the embodiment shown. Handle 40 can be grasped by a user when using dental pick 32. In alternate embodiments, handle 40 can be any shape that can be grasped by the user. A bottom end of handle 40 tapers down to body 42. Body 42 has a thin cylindrical shape in the embodiment shown. A bottom end of body 42 tapers down to tip 46. Bristles 44 are attached to the bottom end of body 42 and extend down to tip 46. Bristles 44 can be made out of a soft rubber material, a plastic material, or a nylon type filament material. Tips 46 and bristles 44 can be used to pick between and around teeth or dental appliances when dental picks 32 are being used.

Dental picks 32 can be separated by breaking connecting ligaments 34 and connecting ligaments 36. Connecting ligaments 34 and connecting ligaments 36 can be broken by slicing them apart, putting pressure on dental picks 32 to break them apart, or folding sheet 30 of dental picks 32 against each other in an alternating pattern to snap them apart.

If done manually, dental picks 32 are typically broken apart by folding one dental pick 32 towards sheet 30 to snap connecting ligament 34 and connecting ligament 36. This can be cumbersome to users, as they have to hold sheet 30 of dental picks 32 and manually snap apart one dental pick 32 every time they want to use a dental pick. It can also be cumbersome to store dental picks 32, especially after sheet 30 of dental picks 32 has been separated into individual dental picks 32. Once dental picks 32 are separated, they can be used in a manner similar to a toothpick or interdental brush to clean between and around teeth and dental appliances. Dental picks 32 can also be used as a substitute for string floss to remove food, bacteria, and other debris from between teeth.

First Embodiment

Figure 2:
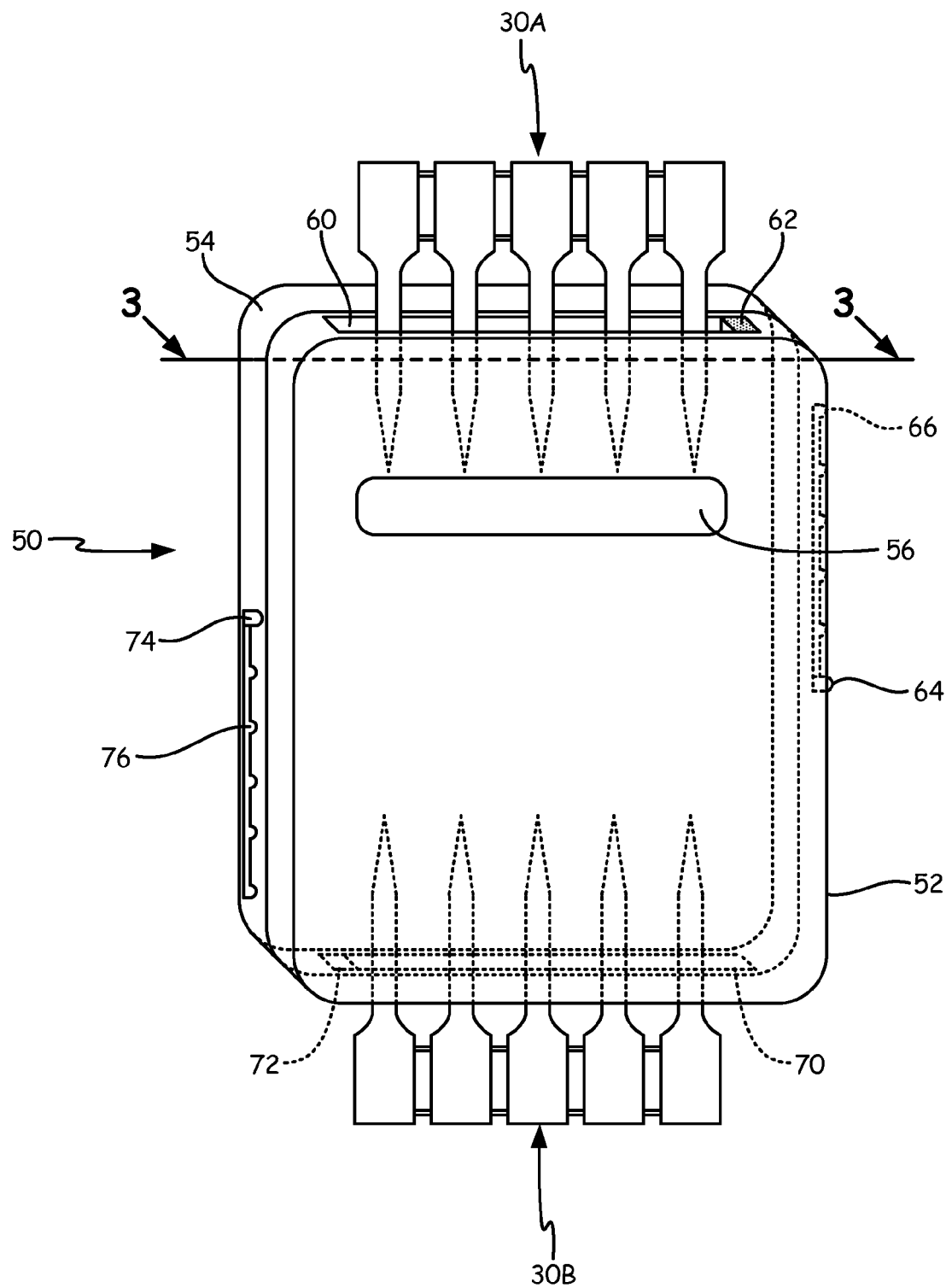
FIG. 2 is a perspective view of a first embodiment of a container when two sheets of dental picks are being loaded.

FIGS. 2-5B illustrate a first embodiment, container 50. FIG. 2 is a perspective view of a first embodiment of container 50 when two sheets 30 (sheet 30A and sheet 30B) of dental picks 32 are being loaded. Container 50 includes first container portion 52, second container portion 54, and window 56. First container portion 52 includes opening 60, door 62, knob 64, and path 66. Second container portion 54 includes opening 70, door 72, knob 74, and path 76.

First container portion 52 and second container portion 54 are connected to one another with fasteners. This can include screws, snap grommets, adhesives, or any other fastener that is capable of holding the two portions together. In the embodiment shown, opening 60 of first container portion 52 is facing upwards, and opening 70 of second container portion 54 is facing downwards. In alternate embodiments, opening 60 of first container portion 52 and opening 70 of second container portion 54 can both face the same direction, or they can face different directions in any arrangement. In alternate embodiments, container 50 may only include first container portion 52. Further, container 50 can be constructed to accommodate sheets 30 of dental picks 32 that include any number of dental picks 32.

First container portion 52 and second container portion 54 each include the same components. Window 56 is located on first container portion 52 to show sheet 30A of dental picks 32 when sheet 30A is loaded into container 50. A similar window can also be located on an outward facing surface of second container portion 54. In the embodiment shown, window 56 has a substantially rectangular shape, but window 56 can have different constructions in alternate embodiments. This can include an oval shaped window, or multiple windows of any shape in front of each stored pick 32 that enable the user to see how many dental picks 32 are in container 50 at any given time.

First container portion 52 includes opening 60 at a top end of container 50. Sheet 30A can be placed in opening 60 and pressed into container 50. Once sheet 30A is loaded, door 62 can be slid into a closed position with knob 64 and path 66. Knob 64 is located in path 66 and slides through path 66 to adjust the position of door 62. Door 62 is in an open position in FIG. 2, allowing sheet 30A to be loaded into container 50. As sheet 30A is loaded into container 50, dental picks 32 will be sliced apart by recessed blades that are held in container 50. The separated dental picks 32 can then be dispensed one at a time, by moving door 62 and providing access to opening 60.

Second container portion 54 includes opening 70 at a bottom end of container 50. Sheet 30B can be placed in opening 70 and pressed into container 50. Once sheet 30B is loaded, door 72 can be slid into a closed position with knob 74 and path 76. Knob 74 is located in path 76 and slides through path 76 to adjust the position of door 72. Door 72 is in an open position in FIG. 2, allowing sheet 30B to be loaded into container 50. As sheet 30B is loaded into container 50, dental picks 32 will be sliced apart by recessed blades that are held in container 50. The separated dental picks 32 can then be dispensed one at a time, by moving door 72 and providing access to opening 70.

Container 50 allows a user to load and separate sheets 30 of dental picks 32. Dental picks 32 can be separated with minimal effort from the user, as all dental picks 32 are separated at the same time when sheet 30 is loaded into container 50. Container 50 will also store dental picks 32 until the user wants to use one. Door 62 and door 72 allow a user to open container 50 to insert sheets 30 and to dispense dental picks 32 one by one, as needed by the user.

Figure 3:
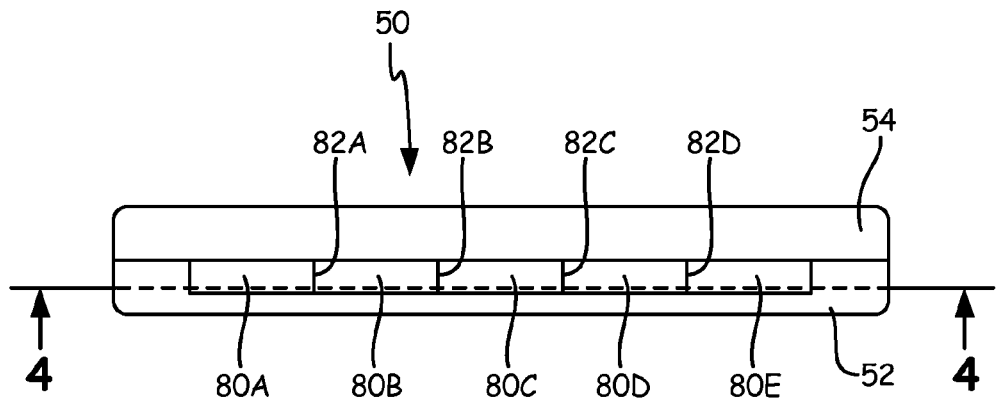
FIG. 3 is a top cross-sectional view of the first embodiment of the container when no dental picks are loaded, taken along line 3-3 of FIG. 2.

FIG. 3 is a top cross-sectional view of the first embodiment of container 50 when no dental picks 32 are loaded, taken along line 3-3 of FIG. 2. Container 50 includes first container portion 52 and second container portion 54. First container portion 52 includes cavities 80 (including cavity 80A, cavity 80B, cavity 80C, cavity 80D, and cavity 80E) and blades 82 (including blade 82A, blade 82B, blade 82C, and blade 82D).

In the embodiment shown, first container portion 52 includes five cavities 80 to receive sheet 30 of dental picks 32. Each cavity 80 has a width at the top that is slightly greater than the width of handle 40 of one dental pick 32 and can receive one dental pick 32 when sheet 30 is loaded. Blades 82 are located between cavities 80 to slice sheet 30 of dental picks 32 when it is loaded. Blade 82A is located between cavity 80A and cavity 80B; blade 82B is located between cavity 80B and cavity 80C; blade 82C is located between cavity 80C and cavity 80D; and blade 82D is located between cavity 80D and cavity 80E. Blades 82 are made out of a thin and rigid material, such as steel or ceramic, and have a sharp edge to slice apart connecting ligaments 34 and connecting ligaments 36 when sheet 30 of dental picks 32 is loaded in container 50.

Figure 4A:
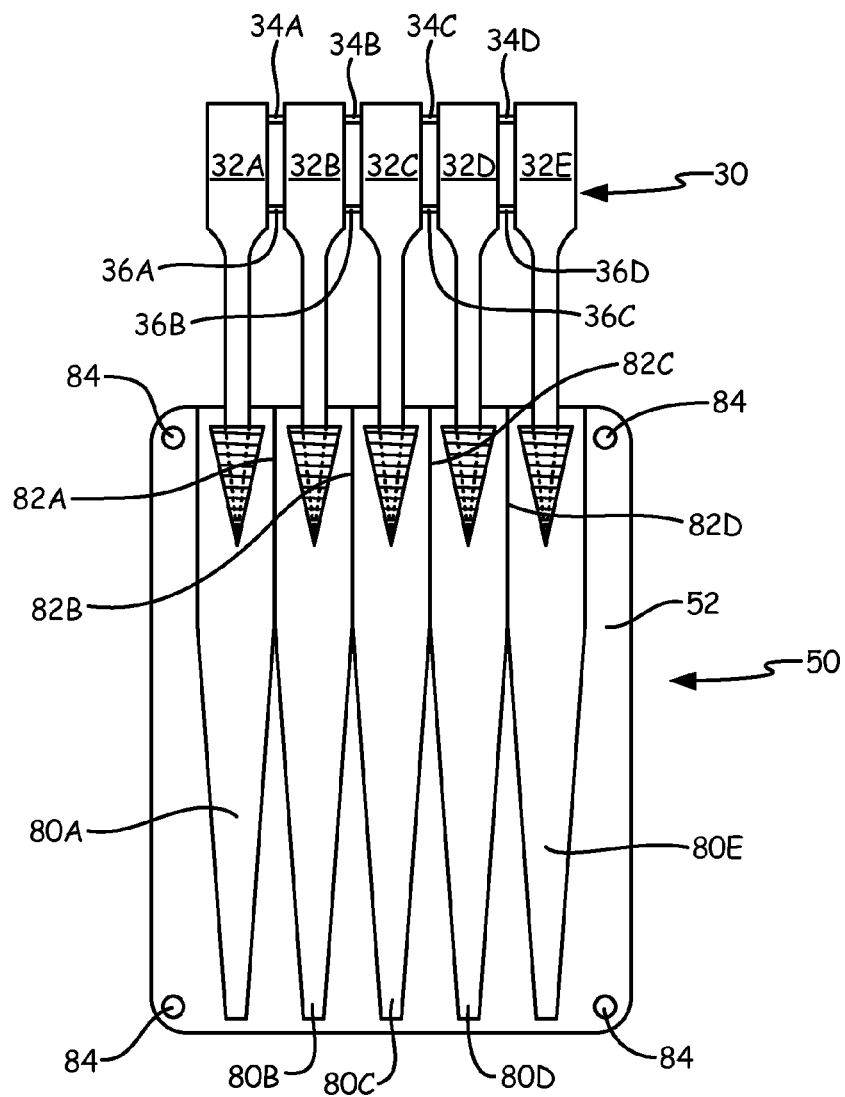
FIG. 4A is a front cross-sectional view of the first embodiment of the container when the sheet of dental picks is being loaded, taken along line 4-4 of FIG. 3.
Figure 4B:
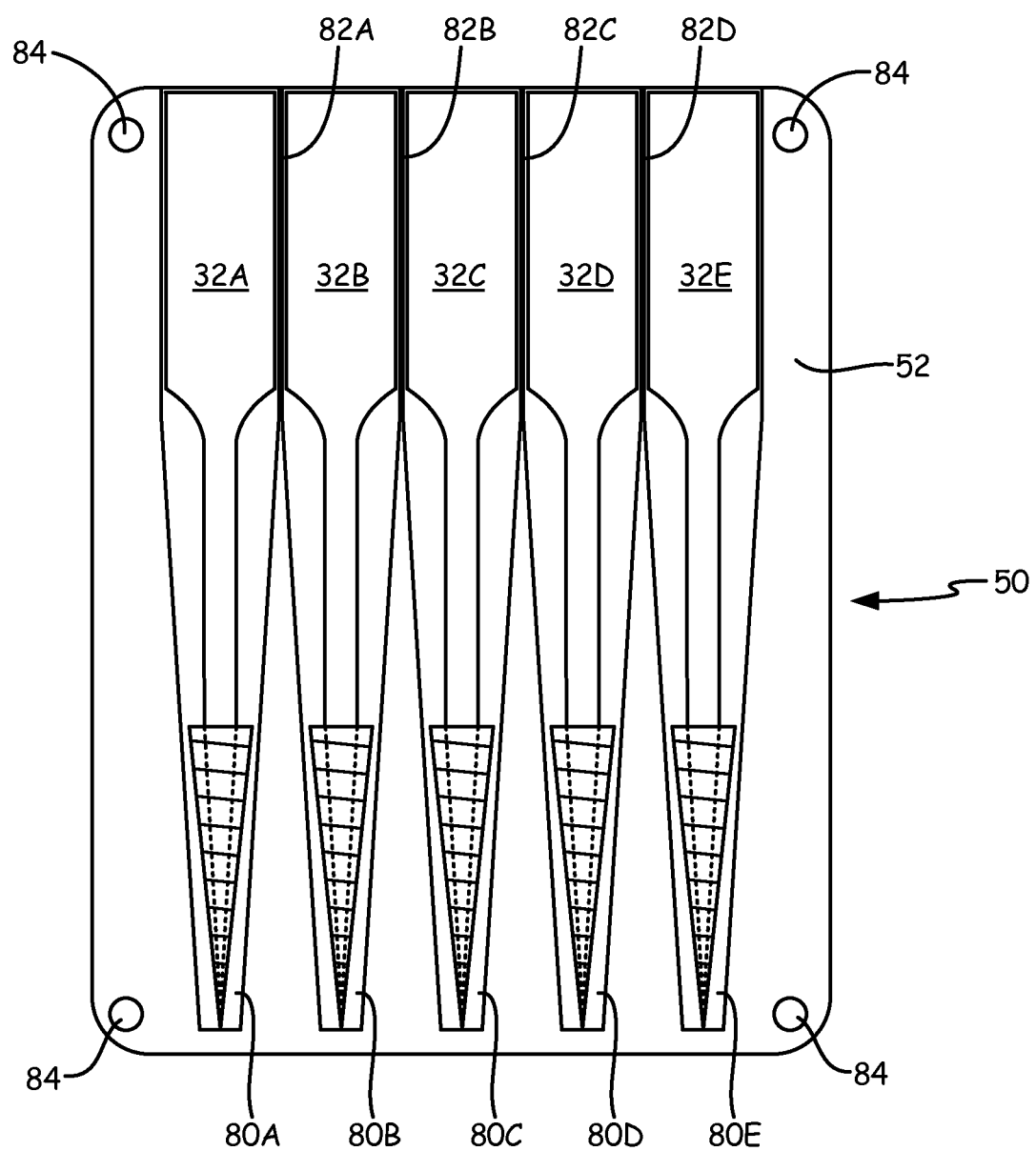
FIG. 4B is a front cross-section view of the first embodiment of the container when the sheet of dental picks is fully loaded, taken along line 4-4 of FIG. 3.

FIG. 4A is a front cross-sectional view of the first embodiment of container 50 when sheet 30 of dental picks 32 is being loaded, taken along line 4-4 of FIG. 3. FIG. 4B is a front cross-section view of the first embodiment of container 50 when sheet 30 of dental picks 32 is fully loaded, taken along line 4-4 of FIG. 3. Sheet 30 includes dental picks 32 (including dental pick 32A, dental pick 32B, dental pick 32C, dental pick 32D, and dental pick 32E), connecting ligaments 34 (including connecting ligament 34A, connecting ligament 34B, connecting ligament 34C, and connecting ligament 34D), and connecting ligaments 36 (including connecting ligament 36A, connecting ligament 36B, connecting ligament 36C, and connecting ligament 36D). Container 50 includes first container portion 52 with cavities 80 (including cavity 80A, cavity 80B, cavity 80C, cavity 80D, and cavity 80E), blades 82 (including blade 82A, blade 82B, blade 82C, and blade 82D), and fasteners 84.

First container portion 52 holds cavities 80 and blades 82. First container portion 52 also includes fasteners 84 at each corner of container 50 to connect first container portion 52 to second container portion 54. In the embodiment shown, fasteners 84 are snap grommets, but in alternate embodiments fasteners 84 can be any fastener that is capable of holding first container portion 52 to second container portion 54. Cavities 80 of first container portion 52 are shaped similar to the shape of dental picks 32 and can receive dental picks 32 when sheet 30 is loaded in container 50. In alternate embodiments, the shape, size, and configuration of dental picks 32 can change, and cavities 80 can be shaped accordingly. Blades 82 are located between cavities 80 to slice connecting ligaments 34 and connecting ligaments 36 when sheet 30 is loaded into container 50. Blade 82A is located between cavity 80A and cavity 80B; blade 82B is located between cavity 80B and cavity 80C; blade 82C is located between cavity 80C and cavity 80D; and blade 82D is located between cavity 80D and cavity 80E.

As seen in FIG. 4A, as sheet 30 is being loaded into first container portion 52 of container 50, dental picks 32 are simultaneously being inserted into cavities 80. Dental pick 32A is loaded into cavity 80A; dental pick 32B is loaded into cavity 80B; dental pick 32C is loaded into cavity 80C; dental pick 32D is loaded into cavity 80D; and dental pick 32E is loaded into cavity 80E. As sheet 30 is pressed into container 50, blades 82 will slice connecting ligaments 34 and connecting ligaments 36. Blade 82A will slice connecting ligament 34A and connecting ligament 36A to separate dental pick 32A from dental pick 32B; blade 82B will slice connecting ligament 34B and connecting ligament 36B to separate dental pick 32B from dental pick 32C; blade 82C will slice connecting ligament 34C and connecting ligament 36C to separate dental pick 32C from dental pick 32D; and blade 82D will slice connecting ligament 34D and connecting ligament 36D to separate dental pick 32D from dental pick 32E.

As seen in FIG. 4B, when sheet 30 is fully loaded into first container portion 52, blades 82 will have separated dental picks 32 into individual pieces. Dental picks 32 are held in cavities 80 after they are separated. Dental pick 32A is held in cavity 80A, dental pick 32B is held in cavity 80B, dental pick 32C is held in cavity 80C, dental pick 32D is held in cavity 80D, and dental pick 32E is held in cavity 80E.

Container 50 allows sheet 30 of dental picks 32 to be separated from one another all at the same time, when sheet 30 is loaded into first container portion 52. As sheet 30 is loaded, blades 82 will slice connecting ligaments 34 and connecting ligaments 36 that hold dental picks 32 together. This decreases the amount of time and effort it takes for a user to separate dental picks 32 for use. Container 50 also provides a way to store dental picks 32 after they have been separated for use at a later time.

Figure 5A:
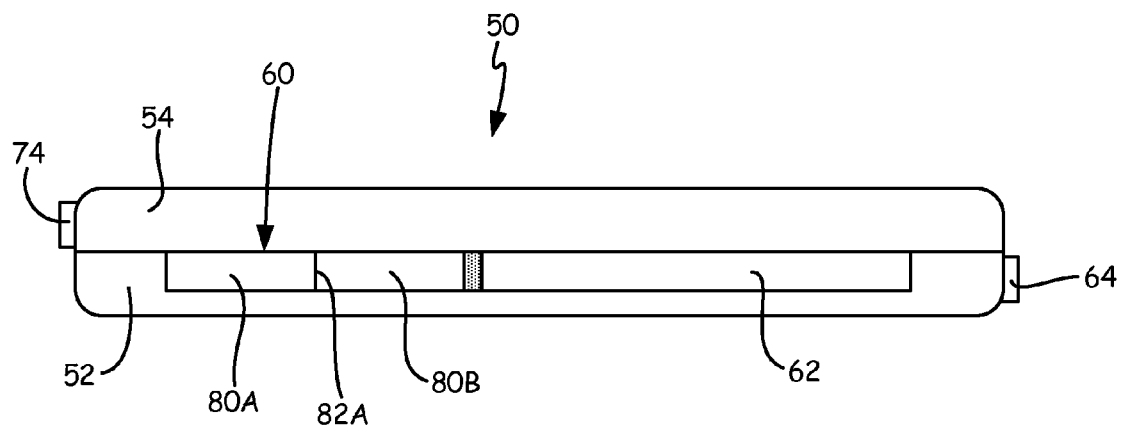
FIG. 5A is a top plan view of the first embodiment of the container.
Figure 5B:
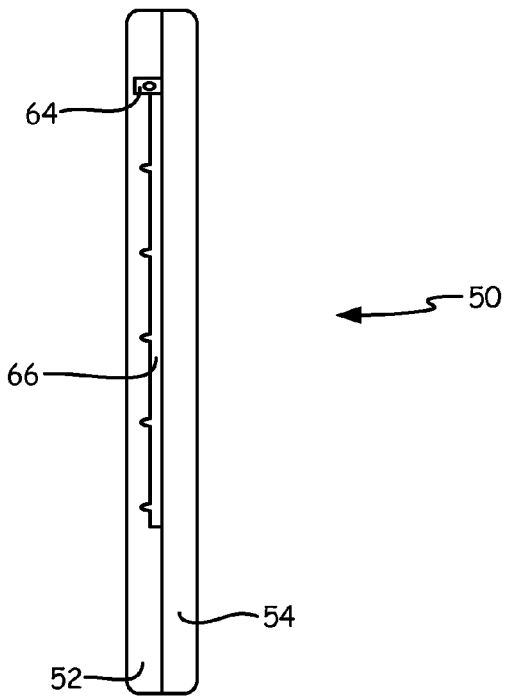
FIG. 5B is a side elevation view of the first embodiment of the container.

FIG. 5A is a top plan view of the first embodiment of container 50. FIG. 5B is a side elevation view of the first embodiment of container 50. Container 50 includes first container portion 52 and second container portion 54. First container portion 52 includes opening 60, door 62, knob 64, path 66, cavity 80A, blade 82A, and cavity 80B. Second container portion 54 includes knob 74.

First container portion 52 is connected to second container portion 54 with a plurality of fasteners. Opening 60 of first container portion 52 is used to load dental picks 32 into first container portion 52. Cavities 80A and 80B are held in first container portion 52 and can receive dental picks 32 when they are loaded. Blade 82A is located between cavity 80A and cavity 80B and can slice apart connecting ligaments 34A and connecting ligaments 36A when sheet 30 of dental picks 32 is loaded into container 50. Door 62 is slidable between a fully open and a fully closed position over cavities 80. Knob 64 and path 66 can be used to slide door 62 between the open and closed positions and can open any number of cavities 80 at a time.

In the embodiment shown, door 62 is a Teflon (polytetrafluorethylene) ribbon. In alternate embodiments, door 62 can be made out of any durable, flexible, and nonporous material that is capable of being positioned in container 50 and that can be slid back and forth between an open and closed position. Door 62 runs along the same side of first container portion 52 that path 66 is located on. As door 62 is opened, it will move down the side of first container portion 52 along path 66. In an alternate embodiment, door 62 may be a rigid plate that slides laterally across the opening, out and away from container 50 to expose cavities 80. Such an embodiment requires that knob 64 be relocated over cavity 80A (when door 62 is in the closed position) to operate door 62, and that path 66 run along opening 60 of first container portion 52, enabling door 62 to protrude beyond container 50.

In a fully open position, sliding door 62 will expose opening 60 and all cavities 80 so that sheet 30 can be loaded into first container portion 52. Once sheet 30 is fully loaded, door 62 can be closed to store dental picks 32 in cavities 80. When a user wants access to a dental pick, they can open door 62 using knob 64 to expose cavity 80A. Knob 64 can slide in path 66 and path 66 has notches designed to catch knob 64. The notches are spaced apart the same width as cavities 80 of container 50. Thus, when knob 64 is moved down one notch, it will only pull door 62 down far enough down to expose cavity 80A.

Once cavity 80A is exposed, container 50 can be tilted downward so that gravity can pull a dental pick towards opening 60. Dental pick 32A in cavity 80A can then be pulled out of container 50 by the user. Door 62 will block the remaining dental picks 32 in the other cavities 80 so that they do not fall out when container 50 is tilted towards the ground. When a user wants access to a second dental pick, they can open sliding door 62 using knob 64 to expose cavity 80A and cavity 80B, as seen in FIG. 5A. Cavity 80A will be empty, but dental pick 32B in cavity 80B can then be dispensed using the same method discussed above. This can continue until all dental picks 32 are dispensed from container 50. This dispensing system allows a user to dispense dental picks 32 one at a time. Door 62 also covers cavities 80 so that dental picks 32 can be stored in a clean environment once they are loaded into container 50.

Second Embodiment

Figure 6:
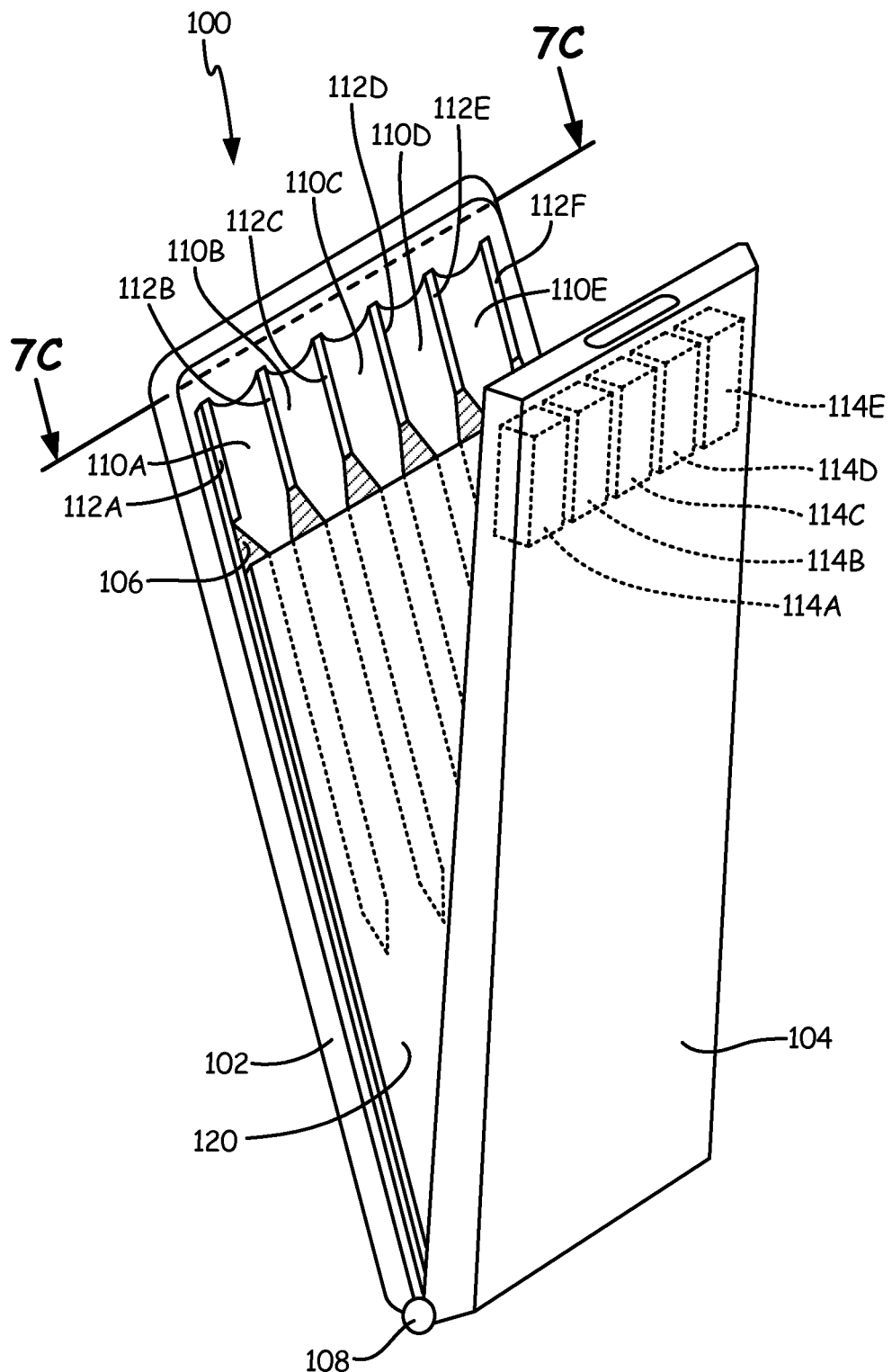
FIG. 6 is a perspective view of a second embodiment of the container in a partially open position.

FIGS. 6-9 illustrate three different versions of a second embodiment, container 100. FIG. 6 is a perspective view of a first version of container 100 in a partially open position. Container 100 includes first container portion 102, second container portion 104, rack 106, and hinge 108. Rack 106 includes cavities 110 (including cavity 110A, cavity 110B, cavity 110C, cavity 110D, and cavity 110E), walls 112 (includes wall 112A, wall 112B, wall 112C, wall 112D, wall 112E, and wall 112F), and cover plate 120. Second container portion 104 includes raised surfaces 114 (including raised surface 114A, raised surface 114B, raised surface 114C, raised surface 114D, and raised surface 114E).

First container portion 102 is connected to second container portion 104 along hinge 108. In the embodiment shown, first container portion 102 and second container portion 104 each form half of container 100. In alternate embodiments, first container portion 102 could form a more substantial portion of container 100 and second container portion 104 could be a lid or a door. Rack 106 is also connected to hinge 108 and is located between first container portion 102 and second container portion 104. Rack 106 has a plurality of cavities 110 and a plurality of walls 112 on it to hold and separate dental picks 32. In alternate embodiments, the dimensions and capacity of container 100 and rack 106 may vary to accommodate different size sheets 30 of varying numbers of dental picks 32. Cavities 110 are shaped similar to the shape of dental picks 32 to hold one dental pick 32 when sheet 30 is loaded into container 100. Cover plate 120 is attached to rack 106 and runs across the front of cavities 110. Cover plate 120 is a rectangular shaped plate that is fastened to rack 106 using any suitable fastener. Cover plate 120 holds dental picks 32 in container 100 in their respective cavities 110 when container 100 is opened and closed along hinge 108. In alternative embodiments, cover plate 120 may be integrated into rack 106 as a single part through various manufacturing applications, such as injection molding. Additionally, cover plate 120 can have varying dimensions as long as its coverage area over cavities 110 is sufficient to secure dental picks 32 in cavities 110. Walls 112 are located above cover plate 120 and between cavities 110 to break sheet 30 of dental picks 32 when it is loaded into container 100. Walls 112 are blunt projections in the embodiment shown, but can be constructed of blades in alternate embodiments. Rack 106 also has a scalloped top edge. The scalloped top edge allows handles 40 of dental picks 32 to protrude out from the top of rack 106 so that a user can easily grasp the handle and pull dental pick 32 out of container 100.

Second container portion 104 includes raised surfaces 114. Raised surfaces 114 are solid square shaped projections in the embodiment shown. In alternate embodiments, raised surfaces 114 can be constructed in any shape that has a sufficient area and protrusion to allow them to be used to place pressure on the handles 40 of dental picks 32. Raised surfaces 114 are sized to fit between walls 112 in cavities 110. When container 100 is closed, raised surfaces 114 put pressure on sheet 30 of dental picks 32 to separate connecting ligaments 34 and connecting ligaments 36 between dental picks 32. This pressure will separate dental picks 32 and each separated pick 32 will be contained in its respective cavity 110.

Container 100 provides a way to separate sheet 30 of dental picks 32 all at one time. This is advantageous, as it prevents the user from having to manually separate one dental pick 32 from sheet 30 each time the users wants to use one dental pick 32. Container 100 can also store the separated dental picks 32 and can be easily opened and closed along hinge 108 to allow a user to remove one dental pick 32 when needed.

Figure 7A:
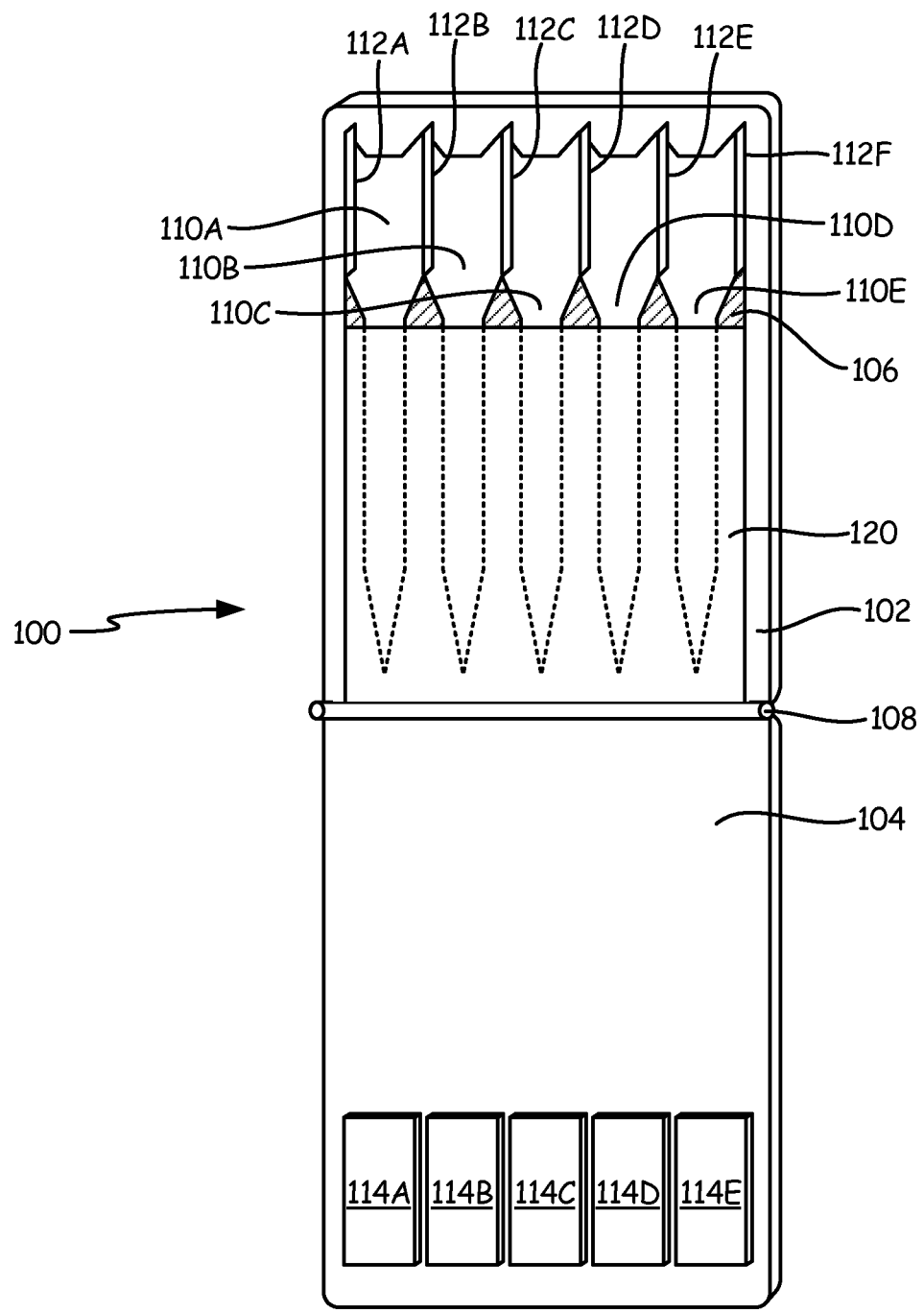
FIG. 7A is a front elevation view of the second embodiment of the container in an open position when no dental picks are loaded.
Figure 7B:
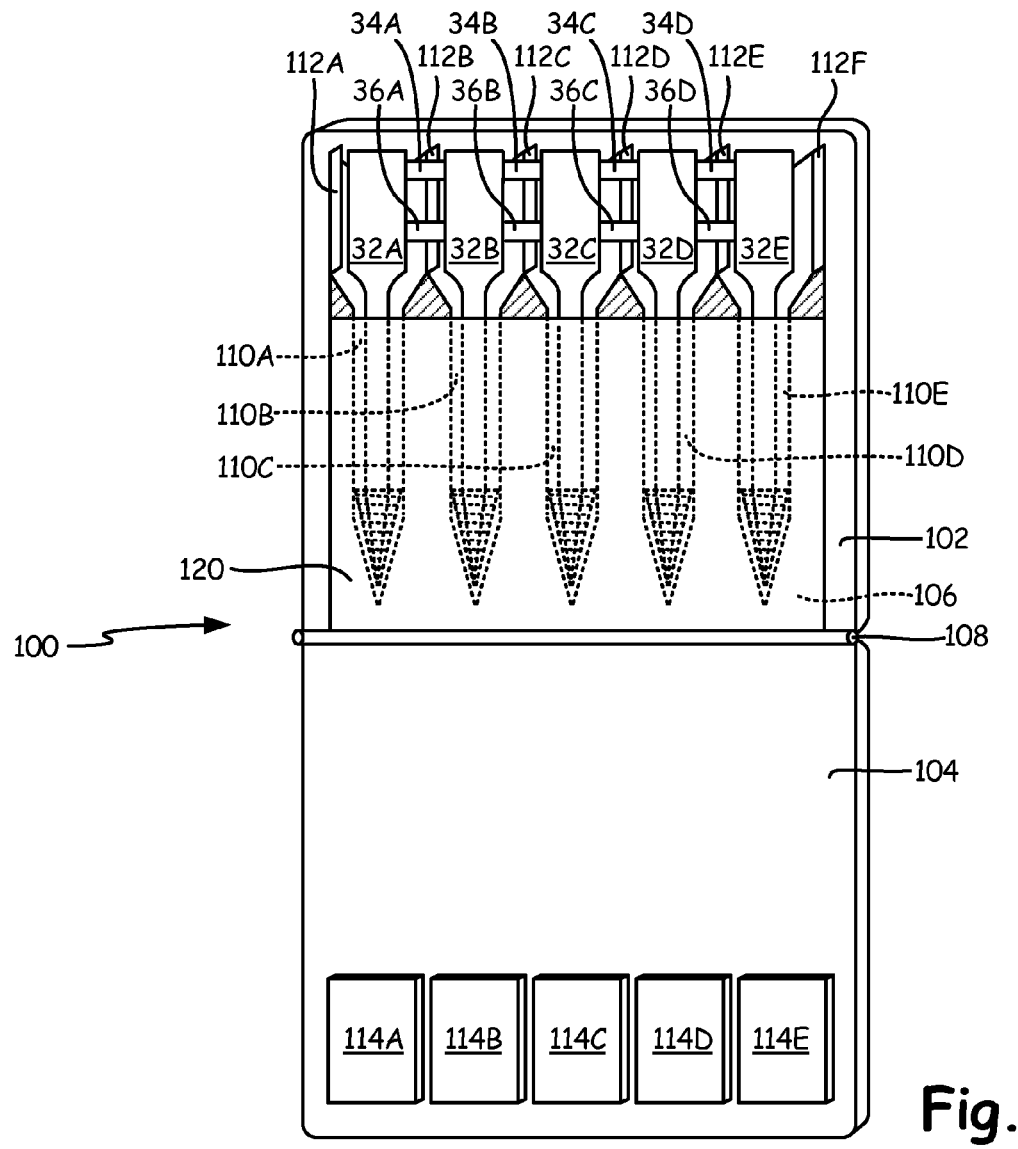
FIG. 7B is a front elevation view of the second embodiment of the container in an open position when a sheet of dental picks is loaded.
Figure 7C:
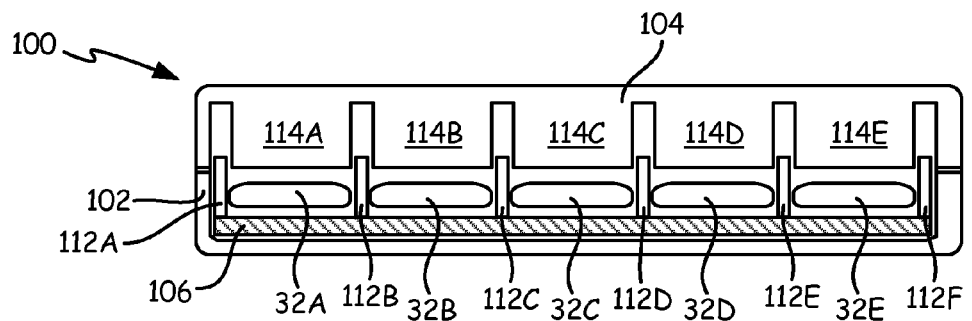
FIG. 7C is a top cross-sectional view of the second embodiment of the container in a closed position, taken along line 7C-7C of FIG. 6.

FIG. 7A is a front elevation view of the second embodiment of container 100 in an open position. FIG. 7B is a front elevation view of the second embodiment of container 100 in an open position when sheet 30 of dental picks 32 is loaded. FIG. 7C is a top cross-sectional view of the second embodiment of container 100 in a closed position, taken along line 7C-7C of FIG. 6. Sheet 30 includes dental picks 32 (including dental pick 32A, dental pick 32B, dental pick 32C, dental pick 32D, and dental pick 32E), connecting ligaments 34 (including connecting ligament 34A, connecting ligament 34B, connecting ligament 34C, and connecting ligament 34D), and connecting ligaments 36 (including connecting ligament 36A, connecting ligament 36B, connecting ligament 36C, and connecting ligament 36D). Container 100 includes first container portion 102, second container portion 104, rack 106, and hinge 108. Rack 106 includes cavities 110 (including cavity 110A, cavity 110B, cavity 110C, cavity 110D, and cavity 110E), walls 112 (includes wall 112A, wall 112B, wall 112C, wall 112D, wall 112E, and wall 112F), and cover plate 120. Second container portion 104 includes raised surfaces 114 (including raised surface 114A, raised surface 114B, raised surface 114C, raised surface 114D, and raised surface 114E).

First container portion 102 is connected to second container portion 104 along hinge 108. Rack 106 is also connected to hinge 108 and is located between first container portion 102 and second container portion 104. Rack 106 has a plurality of cavities 110 and a plurality of walls 112 on it to hold and separate dental picks 32. Wall 112A is located on a first side of cavity 110A; wall 112B is located between cavity 110A and cavity 110B; wall 112C is located between cavity 110B and cavity 110C; wall 112D is located between cavity 110C and cavity 110D; wall 112E is located between cavity 110D and 110E; and wall 112F is located on a second side of cavity 110E. Rack 106 also includes cover plate 120 that is placed on top of cavities 110 and is fastened to rack 106. Cover plate 120 holds dental picks 32 in cavities 110.

Second container portion 104 includes a plurality of raised surfaces 114. Raised surfaces 114 are shaped and sized so that they can be placed between walls 112 and over the pick handles 40 when container 100 is closed. Raised surface 114A can be placed between wall 112A and wall 112B; raised surface 114B can be placed between wall 112B and wall 112C; raised surface 114C can be placed between wall 112C and wall 112D; raised surface 114D can be placed between wall 112D and wall 112E; and raised surface 114E can be placed between wall 112E and wall 112F.

Sheet 30 of dental picks 32 can be placed in container 100 by sliding it downward into cavities 110 between rack 106 and cover plate 120. As seen in FIG. 7B, when sheet 30 is placed in container 100, connecting ligaments 34 and connecting ligaments 36 rest on top of walls 112. Connecting ligament 34A and connecting ligament 36A rest on wall 112B; connecting ligament 34B and connecting ligament 36B rest on wall 112C; connecting ligament 34C and connecting ligament 36C rest on wall 112D; and connecting ligament 34D and connecting ligament 36D rest on wall 112E. Wall 112A and wall 112F are used to align dental picks 32 in container 100. When container 100 is closed, raised surfaces 114 put pressure on handles 40 of dental picks 32. Raised surface 114A comes into contact and puts pressure on dental pick 32A; raised surface 114B comes into contact and puts pressure on dental pick 32B; raised surface 114C comes into contact and puts pressure on dental pick 32C; raised surface 114D comes into contact and puts pressure on dental pick 32D; and raised surface 114E comes into contact and puts pressure on dental pick 32E. Pressing dental picks 32 with raised surfaces 114 will put pressure on connecting ligaments 34 and connecting ligaments 36 that rest on walls 112. This pressure against walls 112 will break connecting ligaments 34 and connecting ligaments 36 to separate dental picks 32. Dental picks 32 will then be pushed into cavities 110. Dental pick 32A will be pushed into cavity 110A; dental pick 32B will be pushed into cavity 110B; dental pick 32C will be pushed into cavity 110C; dental pick 32D will be pushed into cavity 110D; and dental pick 32E will be pushed into cavity 100E.

Using container 100 to break sheet 30 of dental picks 32 is advantageous, as the user no longer needs to manually separate dental picks 32 when the user wants to use one. The user need only place dental picks 32 in rack 106 in container 100 and then close container 100. When container 100 closes, connecting ligaments 34 and connecting ligaments 36 will break apart and dental picks 32 will separate from one another. Dental picks 32 will also be pushed into cavities 110, which will store dental picks 32. When a user wants to use one dental pick 32, the user can open container 100 and pick one dental pick 32 from container 100. Picking one dental pick 32 from container 100 is facilitated with the scalloped upper edge of rack 106, which creates a gap where the user can grasp handle 40 of one dental pick 32. Container 100 makes it easy to separate sheet 30, to store dental picks 32, to dispense dental picks 32.

Figure 8A:
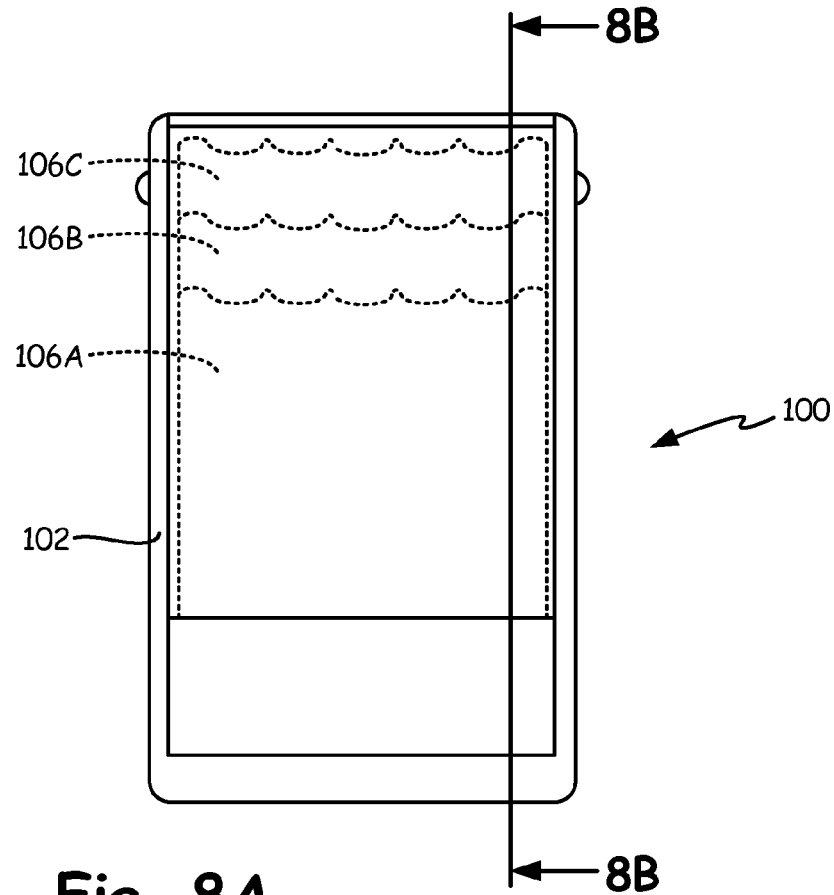
FIG. 8A is a front elevation view of the second embodiment of the container in a closed position.
Figure 8B:
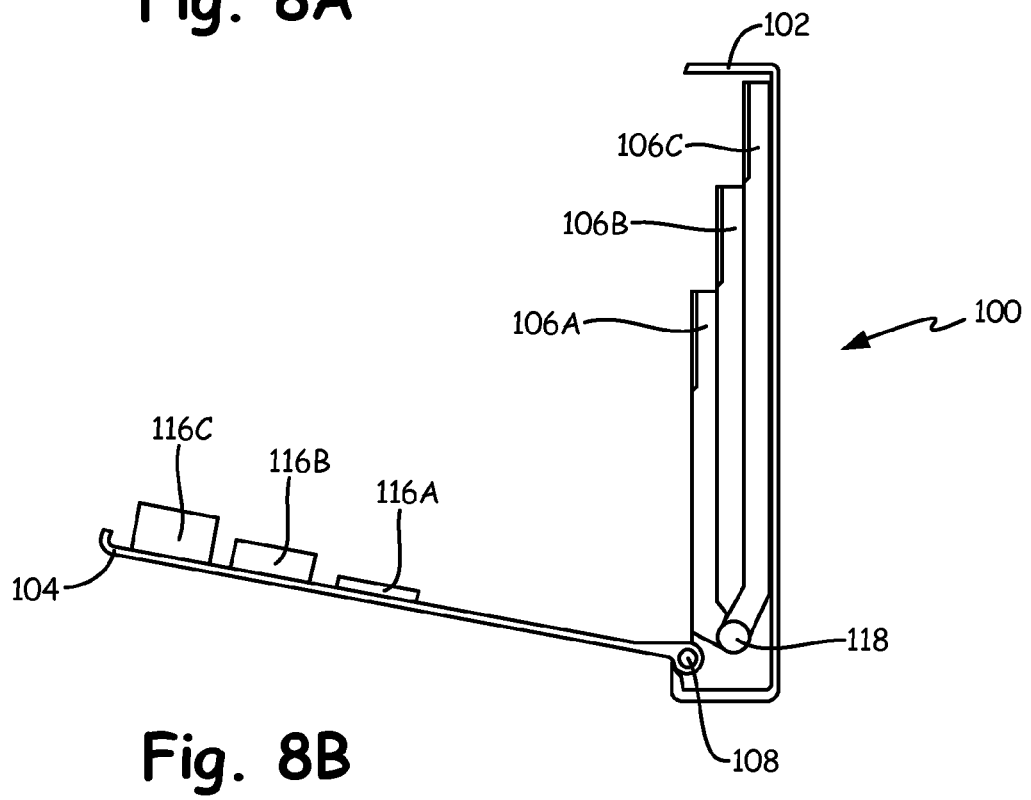
FIG. 8B is a side cross-sectional view of the second embodiment of the container in an open position, taken along line 8B-8B of FIG. 8A.

FIGS. 8A and 8B show a second version of the second embodiment in which container 100 includes multiple racks 106. FIG. 8A is a front elevation view of container 100 with a plurality of racks 106 in a closed position. FIG. 8B is a side cross-sectional view of the second embodiment of container 100 in an open position, taken along line 8B-8B of FIG. 8A. Container 100 includes first container portion 102, second container portion 104, racks 106 (including rack 106A, rack 106B, and rack 106C), raised surfaces 116 (including raised surface 116A, raised surface 116B, and raised surface 116C), hinge 108, and hinge 118.

First container portion 102 and second container portion 104 are connected to one another along hinge 108. In the embodiment seen in FIGS. 8A-8B, first container portion 102 forms the body of container 100 and second container portion 104 is a cover that can be opened and closed by rotating it around hinge 108. Rack 106A, rack 106B, and rack 106C are located in container 100 between first container portion 102 and second container portion 104. Rack 106A is located on a first side of rack 106B; rack 106B is located between rack 106A and rack 106C; and rack 106C is located on a second side of rack 106B. As discussed above in reference to FIGS. 6-7C, each rack will have a plurality of cavities to hold separated dental picks 32 and a plurality of walls to separate dental picks 32 when pressure is applied. Racks 106 are attached at hinge 118. Hinge 118 is held inside container 100 and is attached at opposite ends to first container portion 102 to hold it in place. Second body portion 104 includes raised surfaced 116 that can be used to break sheets 30 of dental picks 32. Raised surfaces 116A can be used to separate dental picks 32 that are carried on rack 106A; raised surfaces 116B can be used to separate dental picks 32 that are carried on rack 106B; and raised surfaces 116C can be used to separate dental picks 32 that are carried on rack 106C. Multiple sheets 30 of dental picks 32 can each be separated apart when container 100 is closed due to the terraced arrangement of raised surfaces 116 and racks 106.

Having a plurality of racks 106 allows container 100 to hold multiple sheets 30 of dental picks 32 at the same time. This increased capacity of dental picks 32 reduces the reloading frequency of container 100 with dental picks 32 by the user. One sheet 30 of dental picks 32 can be loaded onto each rack 106, and when container 100 is closed, all sheets 30 of dental picks 32 that are held in container 100 will break apart.

Figure 9:
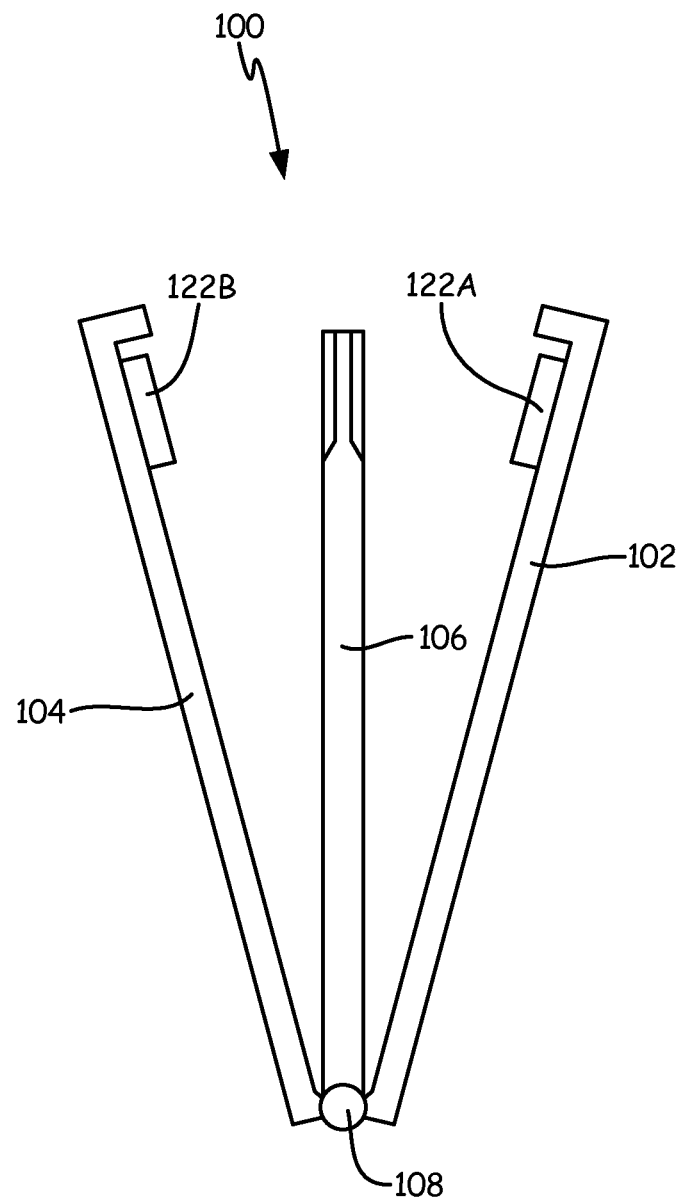
FIG. 9 is a side cross-sectional view of the second embodiment of the container in an open position, taken along line 8B-8B of FIG. 8A.

FIG. 9 is a side cross-sectional view of a third version, with container 100 in an open position. Container 100 includes first container portion 102, second container portion 104, rack 106, and hinge 108. First container portion 102 includes raised surfaces 122A and second container portion 104 includes raised surfaces 122B.

First container portion 102 and second container portion 104 are connected to one another along hinge 108. First container portion 102 and second container portion 104 each form half of container 100. Rack 106 is also connected to hinge 108. Rack 106 includes a first set of walls and cavities on a first side, and a second set of walls and cavities on a second side. This allows rack 106 to hold two sheets 30 of dental picks 32, one sheet 30 on either side. First container portion 102 includes raised surfaces 122A that can be used to separate dental picks 32 that are held on the first side of rack 106. Second container portion 104 includes raised surfaces 122B that can be used to separate dental picks 32 that are held on the second side of rack 106.

The configuration of rack 106 with cavities and walls on two sides allows multiple sheets 30 of dental picks 32 to be loaded and separated in container 100 at one time. This increases the efficiency and convenience of separating dental picks 32 in container 100. The second and third versions of this embodiment also reduce the reloading frequency required by the user due to the increased number of dental picks 32 that can be separated and carried in container 100 at one time.

Third Embodiment

Figure 10:
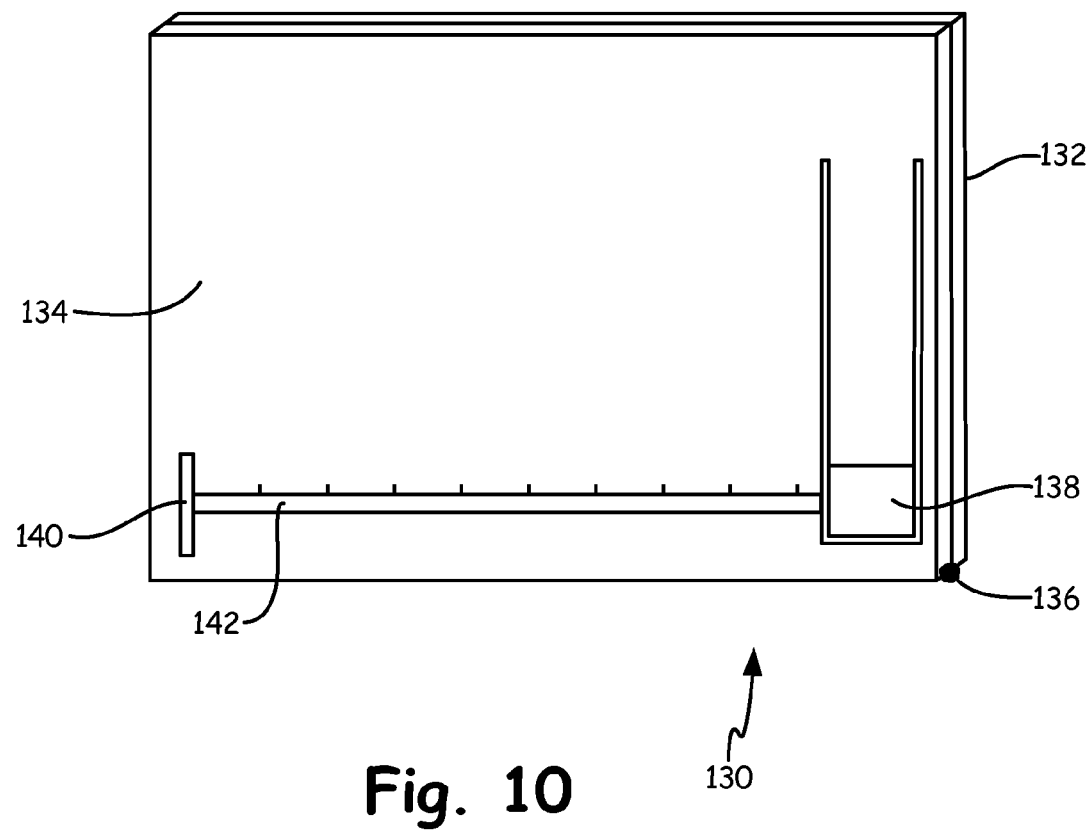
FIG. 10 is a perspective view of a third embodiment of the container in a closed position.
Figure 11A:
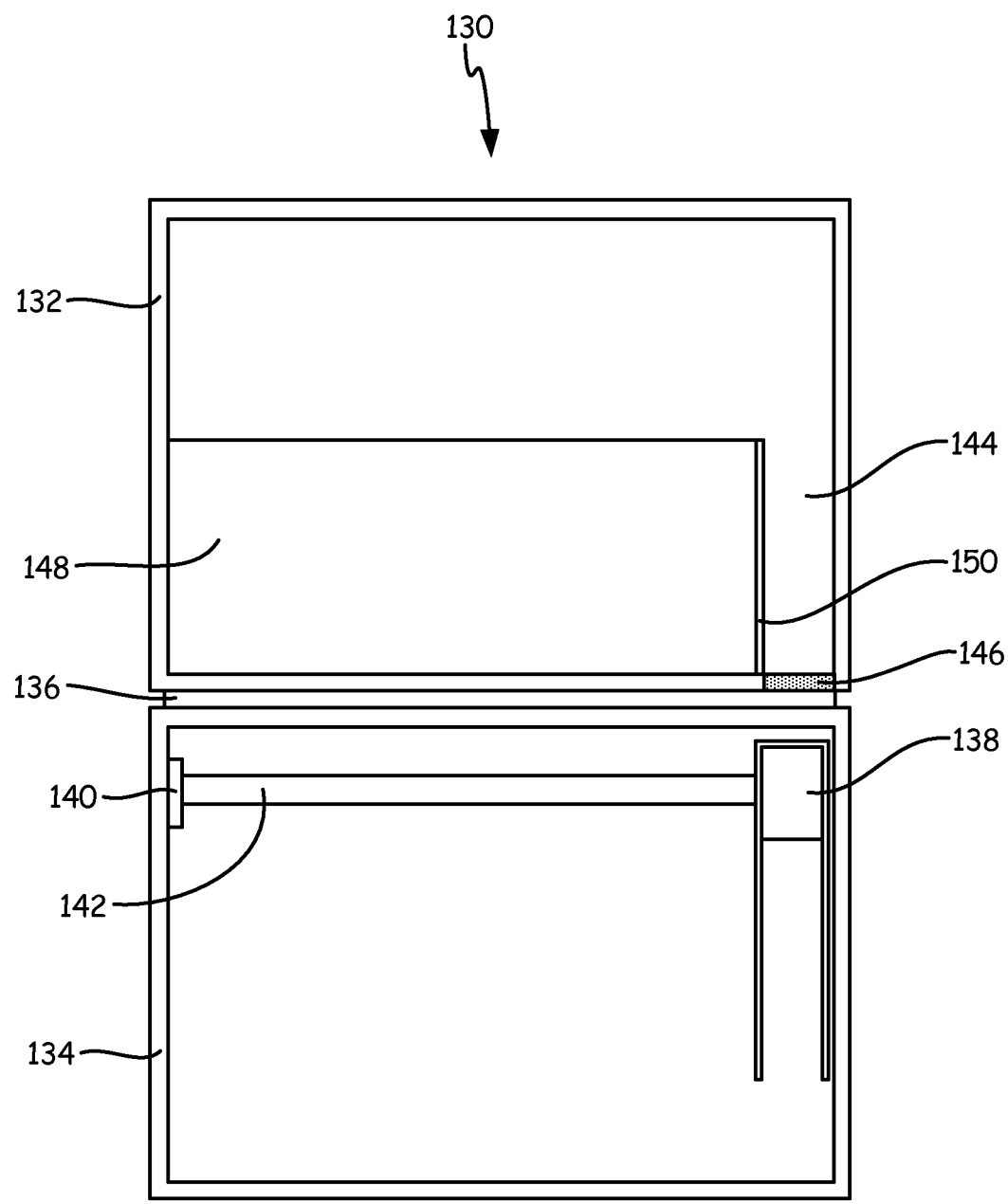
FIG. 11A is front elevation view of the third embodiment of the container in an open position when no dental picks are loaded.
Figure 11B:
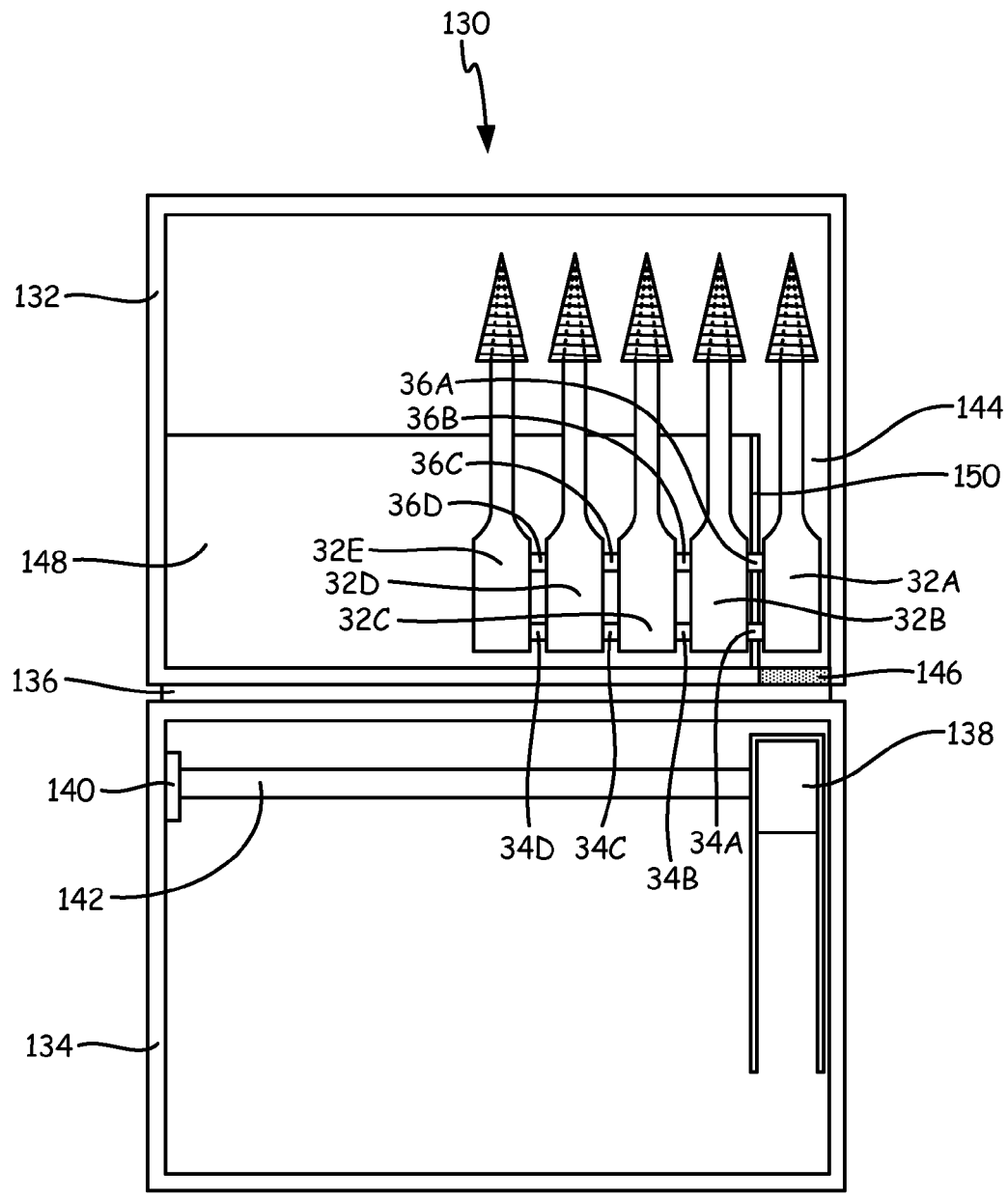
FIG. 11B is a front elevation view of the third embodiment of the container in an open position when a sheet of dental picks is loaded.

FIGS. 10, 11A and 11B illustrate a third embodiment, container 130. FIG. 10 is a perspective view of container 130 in a closed position. Container 130 includes first container portion 132, second container portion 134, hinge 136, lever 138, sliding fence 140, and path 142.

First container portion 132 and second container portion 134 are connected to one another along hinge 136. Hinge 136 can be placed on any side of container 130 in alternate embodiments. In a closed position, first container portion 132 and second container portion 134 form a rectangular shaped container 130. On the face of second container portion 134 there is lever 138, sliding fence 140, and path 142. Lever 138 includes a button at a bottom end that is attached to a body piece. The body piece of lever 138 is attached to second container portion 134 at a top end. The button end of lever 138 can be pressed inwards into container 130 to break one dental pick 32 from sheet 30 at a time. In alternate embodiments, lever 138 can be replaced with a spring-loaded button that can be pressed inwards into container 130. Sliding fence 140 is used to slide sheet 30 of dental picks 32 into position inside container 130 so that each dental pick 32 can be separated by lever 138. Path 142 provides a pathway that sliding fence 140 can slide upon. The positioning of path 142 across second container portion 134 can vary in order to provide the most effective contact point for sliding fence 140 to slide sheet 30. Sliding fence 140 can either be moved manually or automatically advanced with a spring-loaded mechanism.

Container 130 is capable of being sized to fit varying sizes of sheets 30 of dental picks 32. Container 130 allows a user to break one dental pick 32 apart as needed, and the separated dental pick 32 can then be dispensed. This allows container 130 to dispense one dental pick 32 at a time. Container 130 also allows a user to store sheets 30 of dental picks 32.

FIG. 11A is a front elevation view of the third embodiment of container 130 in an open position when no dental picks 32 are loaded. FIG. 11B is a front elevation view of the third embodiment of container 130 in an open position when sheet 30 of dental picks 32 is loaded. Sheet 30 includes dental picks 32 (including dental pick 32A, dental pick 32B, dental pick 32C, dental pick 32D, and dental pick 32E), connecting ligaments 34 (including connecting ligament 34A, connecting ligament 34B, connecting ligament 34C, and connecting ligament 34D), and connecting ligaments 36 (including connecting ligament 36A, connecting ligament 36B, connecting ligament 36C, and connecting ligament 36D). Container 130 includes first container portion 132, second container portion 134, hinge 136, lever 138, sliding fence 140, path 142, exit chute 144, opening 146, raised back 148, and ledge 150.

First container portion 132 and second container portion 134 are connected to one another along hinge 136. First container portion 132 includes raised back 148. Raised back 148 will support and elevate sheet 30 of dental picks 32 when they are loaded in container 130 so bristles 44 do not contact any inside surface of container 130. This will prevent friction and resistance between bristles 44 and container 130 when sheets 30 are slid across raised back 148. First container portion 132 also includes exit chute 144, opening 146, and ledge 150 at a first side of container 130. Exit chute 144 has a width that is slightly larger than the width of handle 40 of one dental pick 32. Exit chute 144 creates an area where one dental pick 32 can be separated from sheet 30 and dispensed from container 130. At one end of exit chute 144 is opening 146. Opening 146 is slightly wider than the width of handle 40 of one dental pick 32. Opening 146 allows one dental pick 32 to be dispensed from container 130, by tilting container 130 with opening 146 facing downward so that gravity can pull dental pick 32 in exit chute 144 out of container 130. Ledge 150 is located at a second side of exit chute 144 and provides a wall upon which one dental pick 32 can be broken off of sheet 30.

Second container portion 134 includes lever 138 that can be pressed inwards into container 130 to break dental picks 32. Second container portion 134 also includes sliding fence 140 and path 142. Sliding fence 140 can move along path 142 to slide sheet 30 of dental picks 32 to the first side of container 130. One dental pick 32 can then be separated in container 130 by positioning sheet 30 of dental picks 32 so that one dental pick 32 is located in exit chute 144. One dental pick 32 can be positioned in exit chute 144 using sliding fence 140. Sliding fence 140 can catch a side edge of sheet 30 and put lateral force against sheet 30 to slide sheet 30 through container 130 until one dental pick 32 is located in exit chute 144. Sliding fence 140 moves along path 142 and can either be moved manually or be spring loaded.

As seen in FIG. 11B, when dental pick 32A is positioned in exit chute 144, the remainder of sheet 30 (including dental pick 32B, dental pick 32C, dental pick 32D, and dental pick 32E) will be positioned on raised back 148. After container 130 is loaded with sheet 30 and closed, lever 138 can be used to break dental pick 32A apart from sheet 30. This happens because lever 138 will put pressure on handle 40 of dental pick 32A. Dental pick 32A is positioned in exit chute 144 so that connecting ligament 34A and connecting ligament 36A are resting on ledge 150. When lever 138 is pressed, dental pick 32A will be forced inwards at handle 40, which will put pressure on connecting ligament 34A and connecting ligament 36A. Connecting ligament 34A and connecting ligament 36A will be broken along ledge 150 due to the pressure from lever 138 that pushes dental pick 32A into exit chute 144, which is at a lower elevation than sheet 30. Once dental pick 32A is separated from sheet 30, container 130 can be tilted with opening 146 facing downwards so that dental pick 32A can fall out of exit chute 144 through opening 146. Once dental pick 32A has been dispensed from container 130, sliding fence 140 will put lateral force on sheet 30 of dental picks 32 and move sheet 30 so that dental pick 32B is positioned in exit chute 144. Dental pick 32B may then be separated from sheet 30, and this process will continue until all dental picks 32 have been dispensed.

Container 130 allows dental picks 32 to be separated from sheet 30 one at a time. Dental picks 32 can also be dispensed one at a time through opening 146. Container 130 is easy to load, by opening container 130 and placing a sheet 30 of dental picks 32 on raised back 148 and to the side of sliding fence 140. Once closed, container 130 is capable of moving one dental pick 32 into exit chute 144 to be separated from sheet 30. Container 130 also stores sheet 30 of dental picks 32, making dental picks 32 easy to access when a user wants to use one.

Fourth Embodiment

Figure 12:
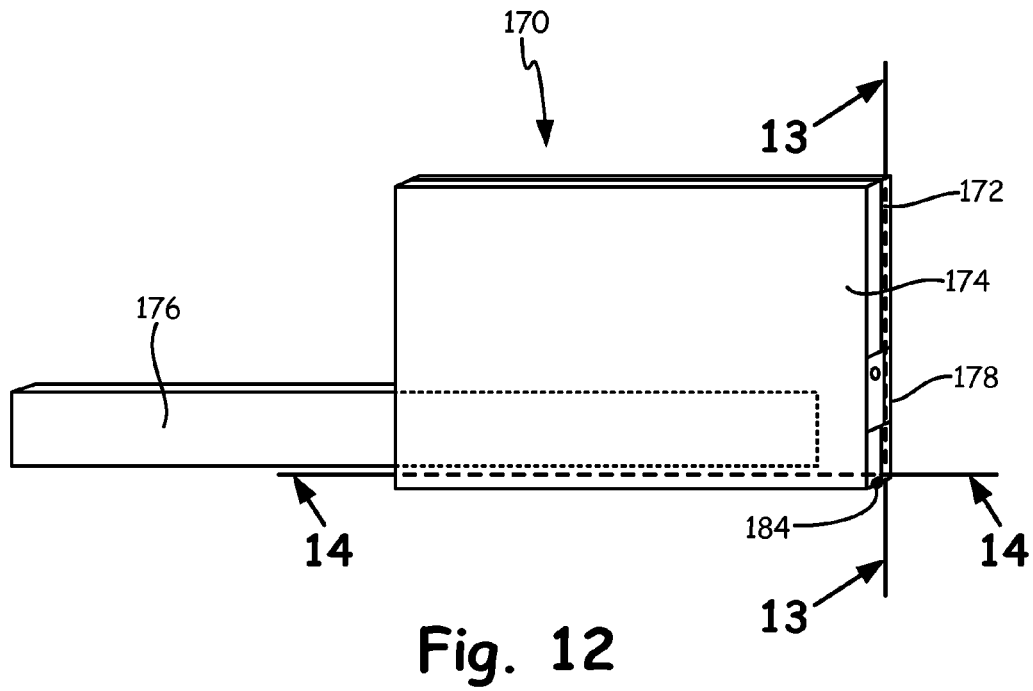
FIG. 12 is a perspective view of a fourth embodiment of the container in a closed position when a push bar is extended.

FIGS. 12-15C illustrate a fourth embodiment, container 170. FIG. 12 is a perspective view of a fourth embodiment of container 170 in a closed position when push bar 176 is extended. Container 170 includes first container portion 172, second container portion 174, push bar 176, hinge 184, and dispenser 178.

First container portion 172 and second container portion 174 are connected to one another along hinge 184. In the embodiment shown, first container portion 172 and second container portion 174 both form half of container 170. In alternate versions, first container portion 172 can form the body of container 170 and second container portion 174 can be a lid that is opened to load sheet 30 of dental picks 32, or any other arrangement that allows a user access to the inside of container 170 so that sheet 30 can be loaded. Container 170 has an inner thickness that is slightly larger than the width of handle 40 of dental picks 32. This allows dental picks 32 to be folded inside container 170 and allows dental picks 32 to rest on one edge of their handles after being separated in container 170. In the embodiment shown, container 170 is capable of receiving multiple sheets 30 of dental picks 32. In alternate versions, container 170 can be constructed to hold one sheet 30 of dental picks 32 and container 170 can be adapted to hold sheets 30 that have varying size and numbers of dental picks 32.

Push bar 176 runs along the bottom end of container 170 and is aligned to make contact with handles 40 of dental picks 32. In an extended position, push bar 176 extends outside of container 170, as seen in FIG. 12. When push bar 176 is extended, sheet 30 of dental picks 32 can be loaded into container 170. After sheet 30 has been loaded, push bar 176 can be pressed inwards to fold sheet 30 in an alternating pattern to snap apart dental picks 32. Push bar 176 can either be manually operated or spring loaded. Container 170 is capable of holding one sheet 30 of dental picks 32 or multiple sheets 30 of dental picks 32, with each sheet 30 being loaded after each previously loaded sheet 30 is compressed and dental picks 32 are snapped apart. Once dental picks 32 have been separated, dispenser 178 can be used to dispense dental picks 32 from the container, one dental pick 32 at a time.

Container 170 allows a user to load, store, and dispense dental picks 32. Sheet 30 can be loaded by placing it in container 170. Dental picks 32 on sheet 30 can then be separated by pushing push bar 176 inwards into container 170. This will cause dental picks 32 to snap apart with minimal effort put forth by the user. Dental picks 32 can then be dispensed by sliding dispenser 178 to provide access to one dental pick 32 at a time.

Figure 13:
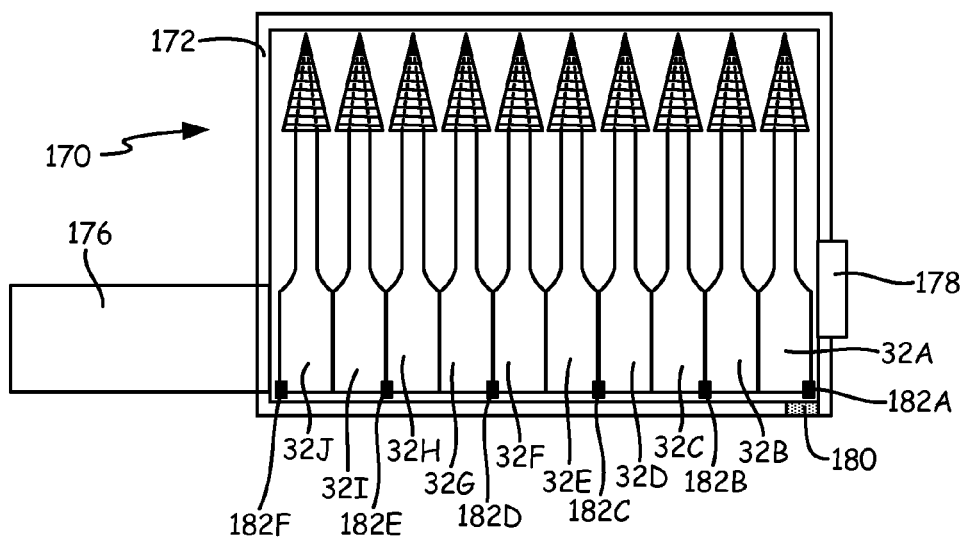
FIG. 13 is a front cross-sectional view of the fourth embodiment of the container in a closed position when the push bar is extended, taken along line 13-13 of FIG. 12.

FIG. 13 is a front cross-sectional view of the fourth embodiment of container 170 in a closed position when push bar 176 is extended and sheet 30 is loaded, taken along line 13-13 of FIG. 12. Sheet 30 includes dental picks 32 (including dental pick 32A, dental pick 32B, dental pick 32C, dental pick 32D, dental pick 32E, dental pick 32F, dental pick 32G, dental pick 32H, dental pick 32I, and dental pick 32J) (sheet 30 of dental picks 32 includes ten dental picks 32 in this embodiment to illustrate the folding action more clearly). Container 170 includes first container portion 172, push bar 176, dispenser 178, opening 180, and joint clips 182 (including joint clip 182A, joint clip 182B, joint clip 182C, joint clip 182D, joint clip 182E, and joint clip 182F).

Push bar 176 runs along the bottom end of container 170 and extends outside of container 170 when it is in an extended position. Dispenser 178 is located at an opposite end of push bar 176 and is used to dispense dental picks 32 through opening 180. Opening 180 is located at a bottom end of container 170 and is sized so that only one dental pick 32 can be dispensed at a time.

First container portion 172 is capable of receiving sheet 30 of dental picks 32. Sheet 30 of dental picks 32 can be loaded either by opening container 170 and placing sheet 30 in first container portion 172, or by opening a lid to container 170 and sliding sheet 30 into container 170. When sheet 30 is loaded into container 170, handles 40 of dental picks 32 should be placed underneath joint clips 182. Joint clip 182A will be placed over an outer edge of handle 40 of dental pick 32A; joint clip 182B will be placed over handle 40 of dental pick 32B and handle 40 of dental pick 32C; joint clip 182C will be placed over handle 40 of dental pick 32D and handle 40 of dental pick 32E; joint clip 182D will be placed over handle 40 of dental pick 32F and handle 40 of dental pick 32G; joint clip 182E will be placed over handle 40 of dental pick 32H and handle 40 of dental pick 32I; and joint clip 182F will be placed over an outer edge of handle 40 of dental pick 32J.

Joint clips 182 are mounted on the inside surface of second container portion 174 so that when container 170 is closed, joint clips 182 will rest on top of sheet 30. In alternate embodiments, joint clips 182 can be mounted on a lid portion of container 170. Joint clips 182 will hold dental picks 32 against an interior surface of first container portion 172 until they are folded by push bar 176. Joint clips 182 can be constructed out a flexible and spring-like material with a high retention memory, as joint clips 182 will be subjected to bending stresses. As dental picks 32 are being folded by push bar 176, joint clips 182 will be pushed out of their normal position by the movement of handles 40 of dental picks 32. Once dental picks 32 are completely folded and separated, joint clips 182 will go back to their original positions due to the high memory nature of the materials used to construct joint clips 182.

Loading container 170 is an easy task for the user. The user need only place sheet 30 of dental picks 32 in container 170 by dropping it into first container portion 172 when second container portion 174 is opened. In an alternate embodiment, sheet 30 can be inserted into container 170 by sliding it in when a lid of container 170 is opened, such as along the bottom edge of container 170. When container 170 is closed, joint clips 182 will be positioned to hold handles 40 of dental picks 32 against the back of first container portion 172. This will facilitate controlled folding of dental picks 32 in an alternating pattern (similar to a paper fan or an accordion) when sheet 30 is compressed by push bar 176.

Figure 14A:
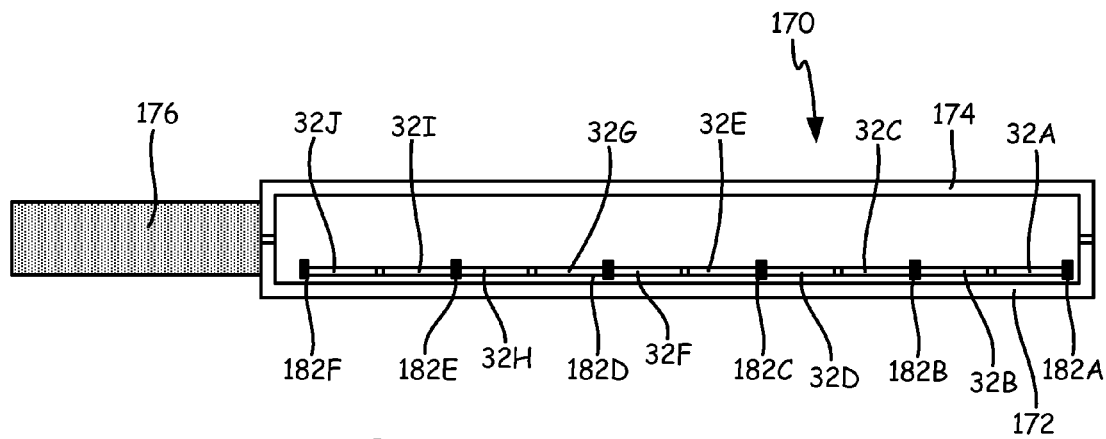
FIG. 14A is a bottom cross sectional view of the fourth embodiment of the container in a closed position when the push bar is extended, taken along line 14-14 of FIG. 12.
Figure 14B:
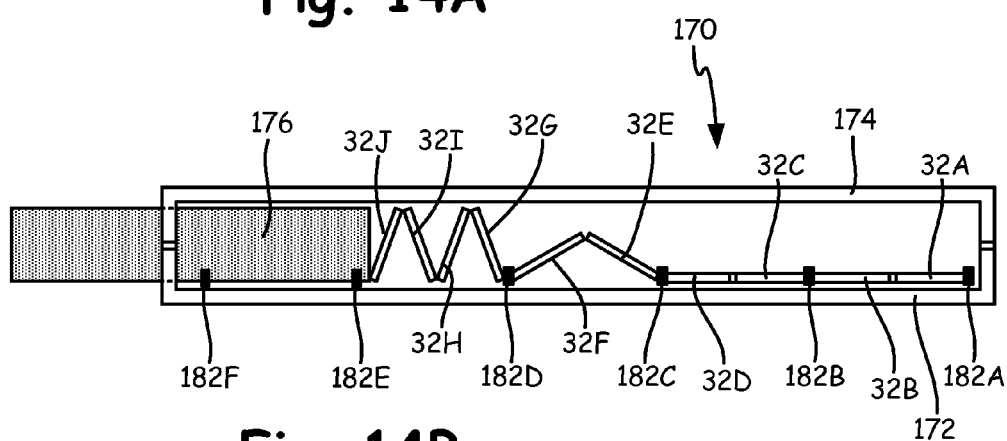
FIG. 14B is a bottom cross-sectional view of the fourth embodiment of the container in a closed position when the push bar is being closed, taken along line 14-14 of FIG. 12.
Figure 14C:
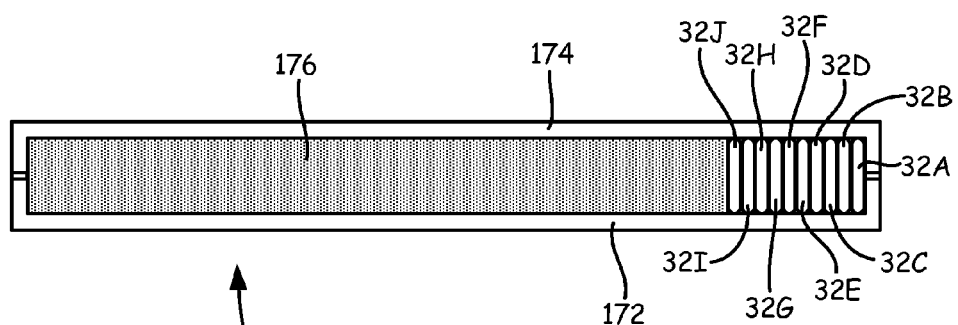
FIG. 14C is a bottom cross-sectional view of the fourth embodiment of the container in a closed position when the push bar is closed, taken along line 14-14 of FIG. 12.

FIG. 14A is a bottom cross-sectional view of the fourth embodiment of container 170 in a closed position when push bar 176 is extended, taken along line 14-14 of FIG. 12. FIG. 14B is a bottom cross-sectional view of the fourth embodiment of container 170 in a closed position when push bar 176 is being closed, taken along line 14-14 of FIG. 12. FIG. 14C is a bottom cross-sectional view of the fourth embodiment of container 170 in a closed position when push bar 176 is closed, taken along line 14-14 of FIG. 12. Sheet 30 includes dental picks 32 (including dental pick 32A, dental pick 32B, dental pick 32C, dental pick 32D, dental pick 32E, dental pick 32F, dental pick 32G, dental pick 32H, dental pick 32I, and dental pick 32J). Container 170 includes first container portion 172, second container portion 174, push bar 176, and joint clips 182 (including joint clip 182A, joint clip 182B, joint clip 182C, joint clip 182D, joint clip 182E, and joint clip 182F).

First container portion 172 and second container portion 174 are connected to one another with a hinge. First container portion 172 has joint clips 182 located along a bottom side to hold dental picks 32 against an interior surface of first container portion 172 when they are folded. Push bar 176 runs along the bottom end of container 170 and extends outside of container 170. Push bar 176 can either be moved manually or spring loaded.

As seen in FIG. 14A, as dental picks 32 are loaded into container 170, handles 40 of dental picks 32 are placed underneath joint clips 182. When dental picks 32 are loaded, push bar 176 is in an extended position. As seen in FIG. 14B, as push bar 176 is pressed inward into container 170, dental picks 32 start to fold up against one another. The arrangement of dental picks 32 resembles a paper fan or an accordion as they are being folded. This folding action will put pressure on connecting ligaments 34 and connecting ligaments 36 between dental picks 32 and will cause dental picks 32 to snap apart from one another. As dental picks 32 are snapped apart, they will collapse onto one another and line up at a first side of container 170, as seen in FIG. 14C.

Container 170 provides the user with an easy way to break dental picks 32. There is minimal effort involved with breaking dental picks 32, as the user need only press push bar 176 inwards into container 170. This will break dental picks 32 apart by folding them upon one another and causing them to snap apart. Container 170 can then also store dental picks 32 and dispense dental picks 32 one at a time.

Figure 15A:
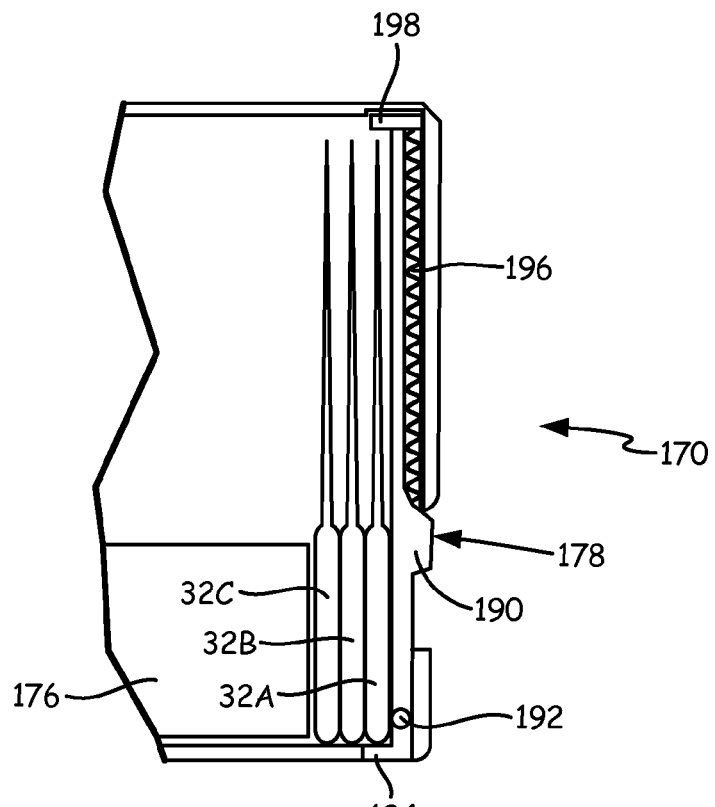
FIG. 15A is a front cross-sectional break-away view of the fourth embodiment of the container after the dental picks have been separated, taken along line 13-13 of FIG. 12.
Figure 15B:
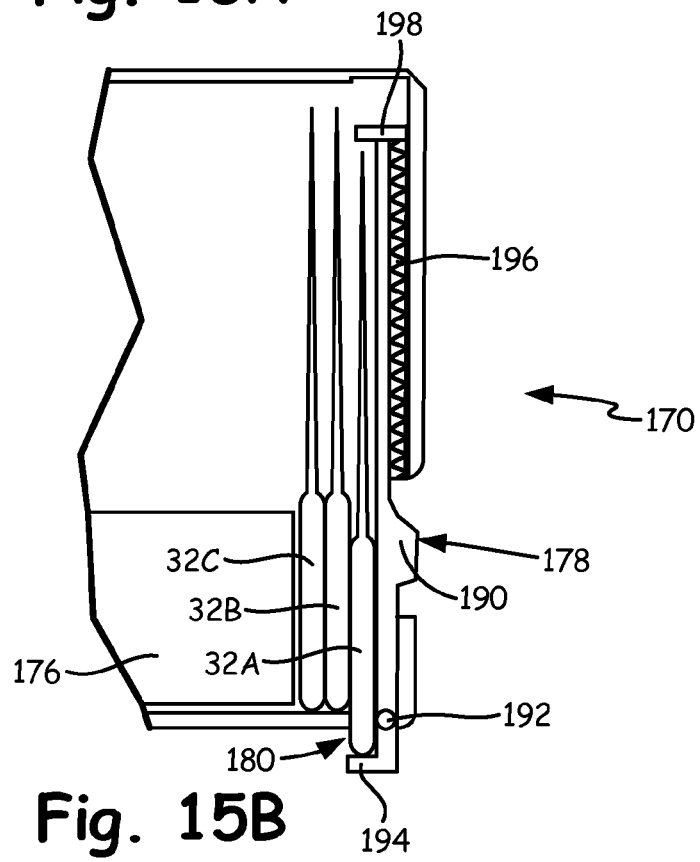
FIG. 15B is a front cross-sectional break-away view of the fourth embodiment of the container as a dental pick is being dispensed, taken along line 13-13 of FIG. 12.
Figure 15C:
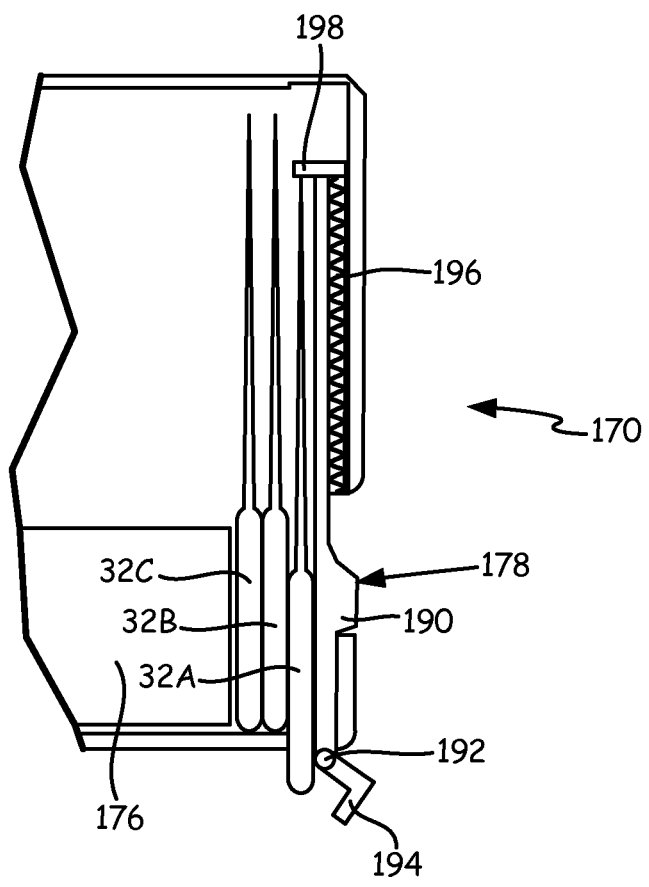
FIG. 15C is a front cross-sectional break-away view of the fourth embodiment of the container as a dental pick is dispensed, taken along line 13-13 of FIG. 12.

FIG. 15A is a front cross-sectional break-away view of the fourth embodiment of container 170 after dental picks 32 have been separated, taken along line 13-13 of FIG. 12. FIG. 15B is a front cross-sectional break-away view of the fourth embodiment of container 170 as dental pick 32 is being dispensed, taken along line 13-13 of FIG. 12. FIG. 15C is a front cross-sectional break-away view of the fourth embodiment of container 170 as dental pick 32 is dispensed, taken along line 13-13 of FIG. 12. Container 170 includes dispenser 178, push bar 176, opening 180, and dental picks 32 (including dental pick 32A, dental pick 32B, and dental pick 32C). Dispenser 178 includes knob 190, hinge 192, lid 194, spring 196, and foot 198.

Container 170 is shown after dental picks 32 have been separated. Dental picks 32 are lined up at a first side of container 170 behind push bar 176. As dental picks 32 are dispensed, push bar 176 will move the next dental pick 32 into position to be dispensed by dispenser 178. Dispenser 178 dispenses dental picks 32 by pulling the handle portion through opening 180 so that the handle portion can be grasped by a user to pull dental pick 32 completely out of container 170.

Dispenser 178 includes knob 190 that can be slid up and down on a first side of container 170. Moving knob 190 downwards will cause one dental pick 32 to be dispensed. When knob 190 is moved upwards, dispenser 178 will reset so that the next dental pick 32 can be moved into position in dispenser 178 by push bar 176. When knob 190 is moved downwards, lid 194 rotates around hinge 192. Hinge 192 includes a spring, which causes lid 194 to flip open when dispenser 178 is activated. Lid 194 will rotate along hinge 192, exposing opening 180 so that dental pick 32 can be dispensed.

After knob 190 is moved downwards, the user can release knob 190 for dispenser 178 to reset. Spring 196 runs parallel to the bottom half of dispenser 178. When knob 190 is moved downwards, spring 196 will be compressed. Then when knob 190 is released, spring 196 will decompress and move dispenser 178 back down into container 170. Foot 198 is located at the top of dispenser 178 and projects outwards from dispenser 178. Foot 198 will catch the tip portion of one dental pick 32 when dispenser 178 is activated. This will cause one dental pick 32 to move downwards in container 170 and will push the handle portion of one dental pick 32 through opening 180. When the handle portion of one dental pick 32 protrudes through opening 180, that dental pick 32 can be grasped by a user and removed from container 170. In an alternate embodiment, foot 198 is two lifting prongs fastened in a fixed position to the dispenser 178, where the prongs straddle body 42 of dental pick 32 just below handle 40. This will move dental pick 32 downwards and through opening 180 when dispenser 178 is activated.

Container 170 is advantageous, as it allows a user to dispense one dental pick at a time as needed by the user. Dispenser 178 works to dispense only one dental pick 32 at a time, and will reset after the user has removed one dental pick 32 from container 170. Container 170 will also break apart and store dental picks 32, until they are needed by the user.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A container for separating, storing, and dispensing dental picks comprising:
   a container to receive a sheet of dental picks, wherein the sheet of dental picks includes multiple interconnected dental picks, and wherein the container comprises:
      a first body portion and a second body portion attached with a first hinge; and
      a rack to hold the dental picks, including hollow cavities on the rack that are each shaped to fit one dental pick;
   a separating device to separate the sheet of dental picks into singular dental picks, wherein the separating device comprises:
      a plurality of walls attached to the rack; and
      a plurality of raised surfaces attached to the second body portion; and
   a dispensing device to dispense the singular dental picks one at a time.

2. The container of claim 1, wherein the rack is connected to the first hinge between the first body portion and the second body portion.

3. The container of claim 1, wherein the rack can be double-sided and hold dental picks on both sides.

4. The container of claim 1, wherein the rack is connected to a second hinge that is attached to the first body portion or the second body portion.

5. The container of claim 1, wherein the container includes a plurality of racks.

6. The container of claim 5, wherein the plurality of racks are connected to the first hinge between the first body portion and the second body portion.

7. The container of claim 5, wherein the plurality of racks are connected to a second hinge that is attached to the first body portion or the second body portion.

8. The container of claim 1, wherein the dental picks are loaded by placing them in the hollow cavities on the rack when the container is in an open position.

9. The container of claim 1, wherein the dental picks are separated by closing the container and pressing the dental picks between the raised surfaces and the plurality of walls.

10. The container of claim 1, wherein the plurality of walls includes a plurality of blades.

11. The container of claim 1, wherein the plurality of walls are located in-between the hollow cavities.

12. The container of claim 1, wherein the dental picks are dispensed by opening the container after the dental picks have been separated.

13. The container of claim 1, wherein the rack has scalloped cut-outs on a top edge to permit the user to grasp the dental picks.

14. The container of claim 1, wherein the raised surfaces are shaped to allow for sufficient area and protrusion to separate the dental picks under pressure when the container is closed.

15. A method for separating and dispensing dental picks comprising:
   obtaining a sheet of dental picks, wherein the sheet of dental picks includes multiple interconnected dental picks;
   loading the sheet of dental picks into a container, wherein the container includes a first body portion and a second body portion;
   positioning the sheet of dental picks on a rack with a plurality of walls that is connected to the container;
   separating the sheet of dental picks into singular dental picks, wherein the dental picks are separated by closing the container and pressing them between the plurality of walls and a plurality of raised surfaces on the second body portion; and
   dispensing the singular dental picks one at a time.

16. The method of claim 15, and further comprising:
   opening the first body portion of the container and the second body portion of the container by rotating them around a hinge; and
   placing the sheet of dental picks in the container.

17. The method of claim 15, wherein opening the container includes opening a first body portion of the container and a second body portion of the container by rotating them around a hinge.

18. The method of claim 15, wherein the dental picks are dispensed by retrieving one dental pick when the container is in an open position.

* * * * *